US009498239B2

(12) United States Patent
Schreck et al.

(10) Patent No.: US 9,498,239 B2
(45) Date of Patent: Nov. 22, 2016

(54) DEVICES AND METHODS FOR INSERTING A SINUS DILATOR

(75) Inventors: Thomas A. Schreck, Palo Alto, CA (US); Jerome E. Hester, Palo Alto, CA (US); Andrew I. Poutiatine, Palo Alto, CA (US); Curtis L. Rieser, Palo Alto, CA (US)

(73) Assignee: SinuSys Corporation, Palo Alto, CA (US)

( * ) Notice: Subject to any disclaimer, the term of this patent is extended or adjusted under 35 U.S.C. 154(b) by 135 days.

(21) Appl. No.: 13/219,497

(22) Filed: Aug. 26, 2011

(65) Prior Publication Data

US 2012/0053404 A1 Mar. 1, 2012

Related U.S. Application Data

(60) Provisional application No. 61/378,360, filed on Aug. 30, 2010, provisional application No. 61/378,368, filed on Aug. 30, 2010, provisional application No. 61/416,240, filed on Nov. 22, 2010, provisional application No. 61/416,248, filed on Nov. 22, 2010.

(51) Int. Cl.
*A61M 29/00* (2006.01)
*A61M 1/00* (2006.01)
(Continued)

(52) U.S. Cl.
CPC ........... *A61B 17/24* (2013.01); *A61B 17/3415* (2013.01); *A61B 17/3468* (2013.01); *A61F 2/186* (2013.01); *A61B 17/3478* (2013.01); *A61F 2210/0061* (2013.01)

(58) Field of Classification Search
CPC .............. A61B 17/24; A61B 17/1688; A61B 17/3415; A61B 17/0057; A61B 17/3468; A61B 17/3478; A61B 2017/1785; A61B 19/24; A61M 29/02; A61M 2029/025; A61M 29/00; A61M 2210/0681; A61M 2210/0618; A61C 8/0092; A61F 2/18–2/186; A61F 2210/0061; A61F 5/08
USPC ......... 600/104; 604/514; 606/191, 192, 199, 606/196
See application file for complete search history.

(56) References Cited

U.S. PATENT DOCUMENTS 3,625,351 A 12/1971 Eisenberg
3,732,865 A 5/1973 Higuchi et al.
(Continued)

FOREIGN PATENT DOCUMENTS

EP 0 923 912 A2 6/1999
JP AH4-215768 2/1994
(Continued)

OTHER PUBLICATIONS

Ronert et al. (2004) "The Beginning of a New Era in Tissue Expansion: Self-Filling Osmotic Tissue Expander—Four-Year Clinical Experience," Plastic and Reconstructive Surgery 114(5)1025-1031.

(Continued)

*Primary Examiner* — Julian W Woo
*Assistant Examiner* — Shaun L David
(74) *Attorney, Agent, or Firm* — Rudy J. Ng; Carol L. Francis; Bozicevic, Field & Francis LLP

(57) ABSTRACT

Devices that are adapted to insert a sinus dilator into a stenotic opening of a paranasal sinus in a subject patient using minimally invasive insertion procedures are provided. The devices and methods can be used to treat sinusitis and other nasal and/or sinus disorders.

29 Claims, 19 Drawing Sheets

600
604
601
603
602
300

(51) Int. Cl.

| | |
|---|---|
| ***A61B 1/233*** | (2006.01) |
| ***A61M 31/00*** | (2006.01) |
| ***A61B 17/24*** | (2006.01) |
| ***A61B 17/34*** | (2006.01) |
| ***A61F 2/18*** | (2006.01) |

(56) References Cited

U.S. PATENT DOCUMENTS 3,760,805 A 9/1973 Higuchi
3,760,984 A 9/1973 Theeuwes
3,786,813 A 1/1974 Michaels
3,845,770 A 11/1974 Theeuwes et al.
4,014,334 A 3/1977 Theeuwes et al.
4,142,526 A 3/1979 Zaffaroni et al.
4,203,440 A 5/1980 Theeuwes
4,203,441 A 5/1980 Theeuwes
4,449,983 A 5/1984 Cortese
4,455,143 A 6/1984 Theeuwes
4,467,806 A 8/1984 Bhiwandiwala et al.
4,480,642 A 11/1984 Stoy et al.
4,663,148 A 5/1987 Eckenhoff et al.
5,160,743 A 11/1992 Edgren et al.
5,234,456 A 8/1993 Silvestrini
5,246,455 A 9/1993 Shikani
5,258,042 A 11/1993 Mehta
5,336,163 A 8/1994 DeMane et al.
5,413,572 A 5/1995 Wong et al.
5,423,745 A 6/1995 Todd et al.
5,464,450 A 11/1995 Buscemi et al.
5,496,368 A 3/1996 Wiese
5,498,255 A 3/1996 Wong
5,499,994 A 3/1996 Tihon et al.
5,500,013 A 3/1996 Buscemi et al.
5,547,378 A 8/1996 Linkow
5,674,241 A 10/1997 Bley et al.
5,693,065 A 12/1997 Rains, III
5,713,855 A 2/1998 Shippert
5,728,396 A 3/1998 Peery et al.
6,123,697 A 9/2000 Shippert
6,224,907 B1 5/2001 Davar et al.
6,270,787 B1 8/2001 Ayer
6,336,496 B1 1/2002 Asai et al.
6,387,124 B1 5/2002 Buscemi et al.
6,455,065 B1 9/2002 Hymes
6,648,873 B2 11/2003 Arenberg et al.
6,753,011 B2 6/2004 Faour
6,976,983 B2 12/2005 Russell
7,014,636 B2 3/2006 Gilbert
7,074,423 B2 7/2006 Fereira et al.
7,108,684 B2 9/2006 Farnan
7,108,762 B2 9/2006 Russell
7,211,076 B2 5/2007 Russell
7,235,068 B2 6/2007 Theeuwes et al.
7,235,099 B1 6/2007 Duncavage et al.
7,241,457 B2 7/2007 Chen et al.
7,361,168 B2 4/2008 Makower et al.
7,410,480 B2 8/2008 Muni et al.
7,419,497 B2 9/2008 Muni et al.
7,462,175 B2 12/2008 Chang et al.
7,500,971 B2 3/2009 Chang et al.
7,520,876 B2 4/2009 Ressemann et al.
7,544,192 B2 6/2009 Eaton et al.
7,591,830 B2 9/2009 Rutter
7,645,272 B2 1/2010 Chang et al.
7,654,997 B2 2/2010 Makower et al.
7,655,257 B2 2/2010 Peery et al.
7,678,099 B2 3/2010 Ressemann et al.
7,678,103 B2 3/2010 Russell
7,740,642 B2 6/2010 Becker
7,740,643 B2 6/2010 Maryanka
2002/0004060 A1 1/2002 Heublein et al.
2002/0088723 A1 7/2002 Lowry et al.
2002/0120276 A1 8/2002 Greene et al.
2003/0171773 A1 9/2003 Carrison
2004/0064150 A1 4/2004 Becker
2004/0073299 A1 4/2004 Hudson et al.
2004/0098095 A1 5/2004 Burnside et al.
2004/0098108 A1 5/2004 Harder et al.
2004/0116958 A1 6/2004 Gopferich et al.
2004/0127871 A1 7/2004 Odorzynski et al.
2004/0243214 A1 12/2004 Farrell
2004/0267241 A1 12/2004 Russell
2005/0054999 A1 3/2005 Morman et al.
2005/0149173 A1 7/2005 Hunter et al.
2005/0165379 A1 7/2005 Mawad
2005/0240147 A1 10/2005 Makower et al.
2005/0268573 A1 12/2005 Yan
2005/0278012 A1 12/2005 Vonderwalde
2006/0047247 A1 3/2006 Anders
2006/0063973 A1* 3/2006 Makower et al. ............ 600/114
2006/0106361 A1 5/2006 Muni et al.
2006/0276831 A1 12/2006 Porter et al.
2007/0005094 A1 1/2007 Eaton et al.
2007/0073269 A1 3/2007 Becker
2007/0084144 A1 4/2007 Labrecque et al.
2007/0106233 A1 5/2007 Huang et al.
2007/0129751 A1 6/2007 Muni et al.
2007/0160647 A1 7/2007 Pritchard et al.
2007/0233036 A1 10/2007 Mandpe
2007/0244562 A1 10/2007 Conner et al.
2007/0250105 A1 10/2007 Ressemann et al.
2007/0269385 A1 11/2007 Yun et al.
2007/0299392 A1 12/2007 Beyar et al.
2008/0044553 A1 2/2008 Freeman et al.
2008/0082045 A1 4/2008 Goldfarb et al.
2008/0097468 A1 4/2008 Adams et al.
2008/0125805 A1 5/2008 Mische
2008/0243140 A1 10/2008 Gopferich et al.
2008/0264102 A1 10/2008 Berra
2008/0292255 A1 11/2008 Stevens et al.
2009/0036968 A1 2/2009 Hepworth et al.
2009/0098184 A1 4/2009 Govil et al.
2009/0125046 A1 5/2009 Becker
2009/0220571 A1* 9/2009 Eaton et al. .................. 424/426
2009/0248141 A1 10/2009 Shandas et al.
2009/0264976 A1 10/2009 Nagasrinivasa
2009/0312745 A1 12/2009 Goldfarb et al.
2009/0314676 A1 12/2009 Peck et al.
2010/0030113 A1* 2/2010 Morriss et al. ............... 600/585
2010/0076269 A1 3/2010 Makower et al.
2010/0099946 A1 4/2010 Jenkins et al.
2010/0100116 A1 4/2010 Brister et al.
2010/0106255 A1 4/2010 Dubin
2010/0155282 A1 6/2010 Govil et al.
2010/0198191 A1 8/2010 Clifford et al.
2010/0305603 A1 12/2010 Nielsen et al.
2010/0312101 A1 12/2010 Drontle et al.
2010/0312338 A1 12/2010 Gonzales et al.
2011/0004057 A1 1/2011 Goldfarb et al.
2011/0021975 A1 1/2011 Covello
2011/0125091 A1 5/2011 Abbate
2012/0053567 A1 3/2012 Schreck et al.
2012/0116350 A1 5/2012 Strauss et al.
2012/0261290 A1 10/2012 Limjaroen et al.
2013/0138132 A1 5/2013 Phee et al.
2013/0231693 A1 9/2013 Edgren et al.
2013/0253564 A1 9/2013 Edgren et al.
2013/0253567 A1 9/2013 Edgren et al.
2013/0261550 A1 10/2013 Edgren et al.
2013/0267987 A1 10/2013 Edgren et al.
2014/0031852 A1 1/2014 Edgren et al.
2014/0358177 A1 12/2014 Schreck et al.
2015/0065810 A1 3/2015 Edgren et al.

FOREIGN PATENT DOCUMENTS

JP AH5-76602 8/1994
WO 9503848 A1 2/1995
WO 9829148 A1 7/1998

(56) References Cited

FOREIGN PATENT DOCUMENTS

| | | | |
|---|---|---|---|
| WO | 9962430 | | 12/1999 |
| WO | 0247558 | A1 | 6/2002 |
| WO | 2005117755 | | 12/2005 |
| WO | 2006034008 | A2 | 3/2006 |
| WO | 2006020180 | | 6/2006 |
| WO | 2007054108 | | 5/2007 |
| WO | 2008008389 | A2 | 1/2008 |
| WO | 2009018248 | A1 | 2/2009 |
| WO | 2010033629 | | 3/2010 |

OTHER PUBLICATIONS

Mazzoli et al. (2004) "Use of self-expanding, hydrophilic osmotic expanders (hydrogel) in the reconstruction of congenital clinical anophthalmos," Database Medline XP002746291, Accession No. NLM15625905, 2 pgs.

Sehgal et al., (1975) "Rapamycin (AY-22,989), a new antifungal antibiotic. 11. Fermentation, isolation and characterization." J. Antibiot 28(10): 727-732. Abstract Only.

* cited by examiner 602
603
607
710
712
608
600

605
MS
601
12
300
662

DEVICES AND METHODS FOR INSERTING A SINUS DILATOR

CROSS-REFERENCES TO RELATED APPLICATIONS

This application claims the benefit of priority under 35 U.S.C. §119(e) to U.S. Provisional Application Nos. 61/378,360 filed Aug. 30, 2010; 61/378,368 filed Aug. 30, 2010; 61/416,248 filed Nov. 22, 2010; and 61/416,240 filed Nov. 22, 2010, the disclosures of each of which are incorporated by reference herein in their entirety.

INTRODUCTION

The bones in the skull and face include a series of air-filled cavities known as paranasal sinuses that are connected by passageways. The paranasal sinuses include frontal sinuses, sphenoid sinuses and maxillary sinuses. The paranasal sinuses are lined with mucus-producing epithelial tissue and are in communication with the nasal cavity. Normally, mucus produced by the epithelial tissue slowly drains out of each sinus through an opening known as an ostium. If the epithelial tissue of one of these passageways becomes inflamed for any reason, the cavities which drain through that passageway can become blocked. This blockage can be periodic (resulting in episodes of pain) or chronic. This interference with drainage of mucus (e.g., occlusion of a sinus ostium) can result in mucosal congestion within the paranasal sinuses. Chronic mucosal congestion of the sinuses can cause damage to the epithelium that lines the sinus with subsequent decreased oxygen tension and microbial growth (e.g., a sinus infection).

The term "sinusitis" refers generally to any inflammation or infection of the paranasal sinuses caused by bacteria, viruses, fungi (molds), allergies or combinations thereof. It has been estimated that chronic sinusitis (e.g., lasting more than 3 months) results in 18 million to 22 million physician office visits per year in the United States. Patients who suffer from sinusitis typically experience at least some of the following symptoms: headaches or facial pain, nasal congestion or post-nasal drainage, difficulty breathing through the nasal cavity, bad breath and/or pain in the upper teeth. Thus, one of the ways to treat sinusitis is by restoring the lost mucus flow.

SUMMARY

Devices that are adapted to insert a sinus dilator into a stenotic opening of a paranasal sinus in a subject patient using minimally invasive insertion procedures are provided. The devices and methods can be used to treat sinusitis and other nasal and/or sinus disorders.

Aspects of the present disclosure include a device for inserting a sinus dilator into a stenotic opening of a paranasal sinus of a patient. In certain embodiments, the device includes: a handheld member including a handle and trigger; a hollow elongated member having a proximal end coupled to the handheld member and a distal end having an opening to an interior cavity of the hollow elongated member; and an interior elongated member extending within the interior cavity of the hollow elongated member, the interior elongated member comprising a retention interface for removably coupling to a sinus dilator, the retention interface positioned outside of the distal end of the hollow elongated member. In some instances, the retention interface is configured to removably couple to the sinus dilator.

In certain cases, the retention interface is relatively displaceable with respect to the hollow elongated member such that at least a portion of the retention interface that is outside of the distal end of the interior elongated member is relatively displaced within the hollow elongated member upon actuation of the trigger.

In some instances, upon actuation of the trigger, the hollow elongated member remains in a relatively fixed position to the handheld member and the retention interface is displaced proximally within the hollow elongated member.

In certain embodiments, the trigger is slidably coupled to the hand held member and coupled to the interior elongated member such that sliding the trigger displaces the retention interface proximally.

Embodiments include that, upon actuation of the trigger, the retention interface remains in a relatively fixed position to the handheld member and the hollow elongated member is displaced distally away from the handheld member.

In some cases, the trigger is slidably coupled to the hand held member and coupled to the hollow elongated member such that sliding the trigger displaces the hollow elongated member distally.

In certain embodiments, the retention interface has a smaller cross-sectional width than a portion of the interior elongated member within the hollow elongated member.

In some instances, the retention interface and the interior elongated material are a single unitary piece of material.

In some cases, the retention interface has a cross sectional width that decreases towards a distal tip of the retention interface.

In certain embodiments, the device includes a light source for illuminating the dilator during insertion.

In certain instances, the retention interface includes a first cylindrically shaped section at a distal end of the retention interface, a second cylindrically shaped section at a proximal end of the retention interface, and a third cylindrically shaped section between the first cylindrically shaped section and the second cylindrically shaped section, where a first cross sectional width of the first cylindrically shaped section is smaller than a third cross sectional width of the third cylindrically shaped section, and where the third cross sectional width of the third cylindrically shaped section is smaller than a second cross sectional width of the second cylindrically shaped section.

In some embodiments, the distal end of the hollow elongated member is curved.

In certain instances, the retention interface comprises a split tip.

In some cases, the device further includes a lumen extending within the interior elongated member and having an opening at the distal tip of the interior elongated member.

In some instances, the lumen is coupled to a fluid source that includes a fluid including at least one drug selected from the group consisting an analgesic, an anesthetic, an anti-inflammatory, an antibiotic, a steroid, and a drug that limits bleeding.

In certain embodiments, the lumen is coupled to a source of suction.

In certain instances, the device includes a sinus dilator removably coupled to the retention interface.

In some embodiments, the interior elongated member is axially rotatable within the hollow elongated member.

In some cases, the hollow elongated member includes a curved tip section at the distal end.

In certain instances, the device includes a sinus dilator with a curved axis removably coupled to the retention interface.

Aspects of the present disclosure also include a method of inserting a sinus dilator in a stenotic opening of a paranasal sinus in a subject. The method includes: coupling a sinus dilator to the retention interface of the interior elongated member of the device described herein; inserting the sinus dilator and distal end of the hollow elongated member of the device into a nasal cavity of the subject; positioning the sinus dilator into the stenotic opening; decoupling the retention interface from the sinus dilator; and removing the hollow elongated member of the device from the nasal cavity of the subject.

In certain embodiments, decoupling the retention interface includes relatively displacing the interior elongated member with respect to the hollow elongated member such that at least a portion of the retention interface that is outside of the distal end of the interior elongated member is relatively displaced within the hollow elongated member, where the sinus dilator is decoupled from the retention interface during the relative displacement and maintained in the stenotic opening.

In some cases, the relative displacing of the interior elongated member with respect to the hollow elongated member includes proximally displacing the retention interface within the hollow elongated member while the hollow elongated member remains in a relatively fixed position to the handheld member.

In some instances, the relative displacing of the interior elongated member with respect to the hollow elongated member includes distally displacing the hollow elongated member away from the handheld member while the retention interface remains in a relatively fixed position to the handheld member.

In certain embodiments, the method includes dispensing fluid to the nasal or sinus cavity via a lumen positioned within the hollow elongated member, where the fluid includes at least one drug selected from the group consisting of an analgesic, an anesthetic, an anti-inflammatory, an antibiotic, a steroid, and a drug that limits bleeding.

In some cases, the method includes suctioning fluid or debris from the nasal cavity or sinus cavity via a lumen positioned within the hollow elongated member.

In some instances, the includes visualizing the stenotic opening via a camera positioned near the distal end of the hollow elongated member.

In certain cases, the method includes illuminating the sinus dilator during the positioning thereof into the stenotic opening.

In some embodiments, the method includes rotating the interior elongated member within the hollow elongated member such that the sinus dilator is reoriented.

In some cases, the hollow elongated member includes a curved tip section at the distal end.

In certain instances, the sinus dilator has a curved axis and the rotation of the interior elongated member angles the sinus dilator in a different orientation.

Aspects of the present disclosure also include a kit that includes: an insertion device according to embodiments described herein; and a sinus dilator adapted to removably couple to the retention interface at the distal end of the implantation device.

In certain embodiments, the kit includes a fluid source adapted to couple to the device and provide fluid to be dispensed out of the device into a sinus or nasal cavity of the subject.

In some instances, the kit includes one or more retention interfaces that may be removably coupled to the interior elongated member of the device.

In some cases, the sinus dilator is coupled to the device.

In certain embodiments, the kit includes one or more sinus ostium sizing probes, the probes being adapted to be removably mounted on the distal end of the hollow elongated member of the device.

DETAILED DESCRIPTION

Devices

Figure 1:
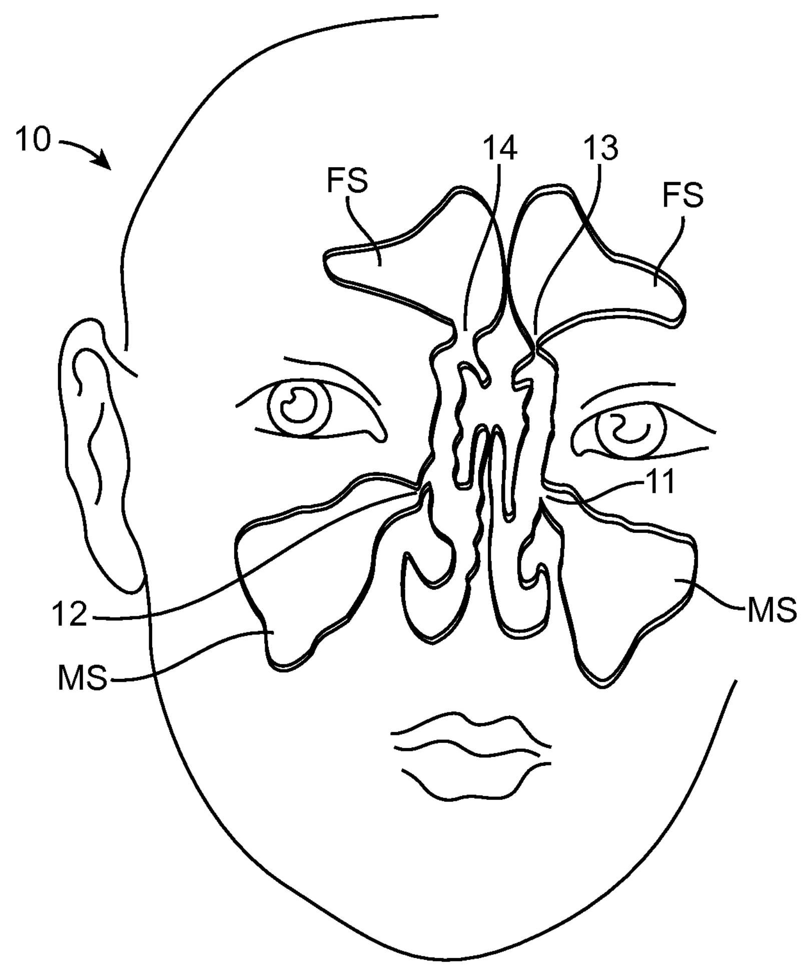
FIG. 1 is a partial cutaway view of a human head showing the positions of the frontal sinuses (FS) and the maxillary sinuses (MS)
Figure 2:
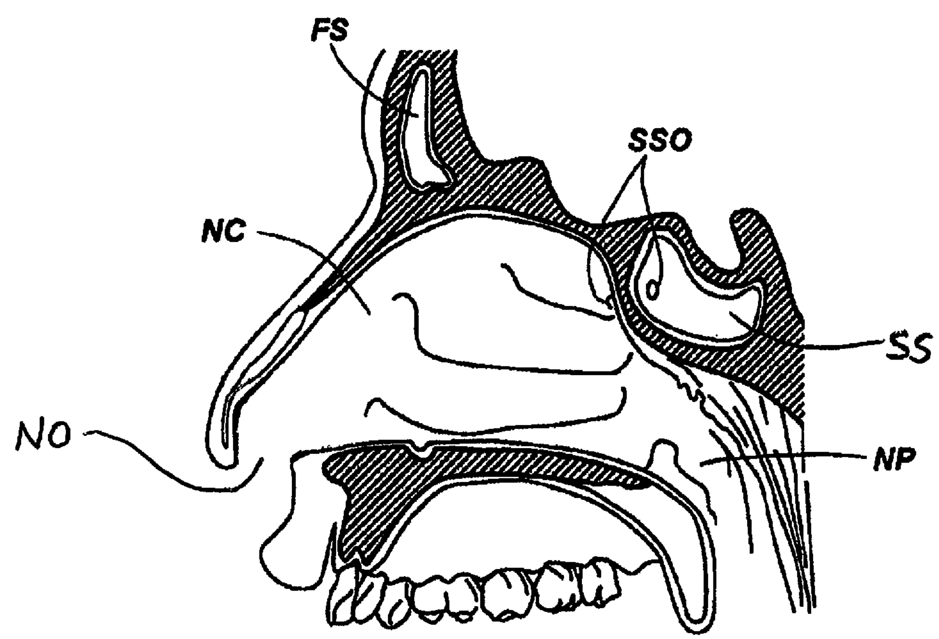
FIG. 2 is a sectional view of a portion of a human head showing the positions of the frontal sinus (FS) and the sphenoid sinus (SS)

FIGS. 1 and 2 illustrate a human patient's nose and sinuses, which may assist in the following description. Referring now to FIG. 1, there is shown a human patient 10 having two frontal sinuses (FS) and two maxillary sinuses (MS). Each of these four sinuses has an opening which can be accessed by way of the patient's nasal cavity. The openings include maxillary sinus openings 11 and 12, of which opening 11 is shown in a normal open condition and opening 12 shown in an occluded or stenotic condition. Similarly, the patient 10 has frontal sinus openings 13 and 14, of which opening 14 is shown in a normal open condition and opening 13 is shown in an occluded or stenotic condition. Referring now to FIG. 2, there is shown a sectional view of a patient's nose and sinuses including the nasal cavity (NC), the nasospharynx (NP), the nasal cavity opening (NO), the frontal sinus (FS), the sphenoid sinus (SS) and the sphenoid sinus opening (SSO).

Aspects of the present disclosure include handheld implantation devices for inserting a sinus dilator into a stenotic opening of a paranasal sinus of a patient. The terms "insert" or "insertion" and "implant" or "implantation" are used herein interchangeably to describe the positioning of a device in a stenotic opening of a subject for a period of time.

The implantation device includes a handheld member coupled to a hollow elongated member. In certain embodiments, the proximal end of the hollow elongated member may be coupled to a handheld member and the distal end of the elongated member is dimensioned to pass through a nasal cavity of a subject. A sinus dilator may be coupled to the distal end of an implantation device, which may then be inserted into the nasal cavity of a subject. The sinus dilator is then positioned within a stenotic opening, which may be partially or completely occluded. In some instances, sinus dilator may include an anchor at the distal end of the sinus dilator that resides within the sinus cavity when the sinus dilator is positioned within the stenotic opening. The anchor secures the sinus dilator from falling back out of the stenotic opening.

In certain embodiments, the implantation devices also include an interior elongated member positioned within the hollow elongated member and extending at least a portion of the length of the hollow elongated member. The interior elongated member has a proximal end coupled to the handheld member and dimensioned to fit within the hollow elongated member. The distal end of the interior elongated member includes a retention interface that is positioned outside of the hollow elongated member and removably couples to a sinus dilator. The sinus dilator may be coupled to the retention interface (e.g., slid on, snapped on, clamped on, etc.) and then the distal end of the implantation device inserted within the nasal cavity to position the sinus dilator within the stenotic opening. As the retention interface and sinus dilator are removably coupled, the sinus dilator may be decoupled and left within the stenotic opening.

The retention interface may include various coupling mechanisms to retain the sinus dilator coupled to the implantation device. In some instances, the retention interface is sized and shaped to fit within a sinus dilator, e.g., within the central passageway of the sinus dilator, or some other passageway, recess, slot, etc. within the sinus dilator. The retention interface may provide sufficient retention to maintain the sinus dilator coupled while permitting some light axial and off-axis loads or bending moments. In some instances, the sinus dilator is sufficiently rigidly affixed to the retention interface to enable a user (e.g., physician) to push the sinus dilator through a stenotic opening even when the opening is completely shut.

As summarized above, the implantation device also includes a handheld member. As the handheld member is held by the user, it is configured to have a shape and size that is amenable to gripping by the user's hand. The implantation device may include, for example, a trigger that is conveniently located for the user to actuate the trigger in order to decouple a sinus dilator coupled to the distal end of the implantation device. For instance, the implantation device may be shaped and sized to be gripped by a physician's hand with trigger accessible to the user's hand while gripping the handheld member, e.g., actuated by the physician's thumb, actuated by a user's index finger with a gun-like trigger, etc. The trigger may, for example, be configured to couple to the interior elongated member or hollow elongated member. It should be appreciated that an electrical circuit can be created to actuate the mechanical translation of the interior elongated member or hollow elongated member.

Upon activation of the trigger, the retention interface is decoupled from the sinus dilator. For example, the interior elongated member may be relatively displaced with respect to the hollow elongated member. In some embodiments, the relative displacing of the interior elongated member with respect to the hollow elongated member includes proximally displacing the retention interface within the hollow elongated member while the hollow elongated member remains in a relatively fixed position to the handheld member. For example, the actuation of the trigger may cause the retention interface to displace such that at least a portion of the retention interface that is outside of the distal end of the interior elongated member is displaced within the hollow elongated member. In some instances, the distal tip of the hollow elongated member may push against the sinus dilator as all or part of the retention interface is displaced within the hollow elongated member.

In other embodiments, the relative displacing of the interior elongated member with respect to the hollow elongated member includes distally displacing the hollow elongated member away from the handheld member while the retention interface and interior elongated member remain in a relatively fixed position to the handheld member. For example, the implantation device may include coupling mechanism, such as a notch on a trigger arm that mates with a protrusion on the hollow elongated member. As the trigger is slidably displaced in a slot on the handheld member, the hollow elongated member is displaced distally away from the handheld member causing the distal tip of the hollow elongated member to push the sinus dilator as all or part of the retention interface is displaced within the hollow elongated member.

The overall weight of the implantation device may take into account usability as a handheld device by the user, e.g., to permit a physician to easily handle hold and handle the device during an implantation procedure. The shape of the handheld member may vary, but in some instances may be in the shape of a wand with a button or switch trigger, gun-like handle and trigger, or other graspable and usable shape.

As summarized above, the implantation devices are dimensioned such that at least the distal end of the devices can pass through the nasal cavity of a subject. The distal end may include, for example, at least a portion of the hollow elongated member, interior elongated member and retention interface. As such, at least the distal end of the device has a cross-sectional diameter that is 10 mm or less, such as 8 mm or less, and including 5 mm or less. The elongated members may have the same outer cross-sectional dimensions (e.g., diameter) along its entire length. Alternatively, the cross-sectional diameter may vary along the length of the elongated members.

Furthermore, as the lengths of the hollow elongated member and interior elongated member may vary. For example, the lengths of the members may vary depending on the specific sinus being targeted. In some instances, the lengths of the elongated members range from 1 cm to 20 cm, such as 2 cm to 15 cm, including 5 cm to 10 cm. It should be appreciated that in some instances the hollow elongated member and interior elongated member may have different lengths from one another.

As stated above, the hollow elongated member and interior elongated member of the implantation devices have a proximal end and a distal end. The term “proximal end”, as used herein, refers to the end of the elongated members (or the implantation device or other component on the implantation device) that are nearer the user (such as a physician operating the device in an implantation procedure), and the term “distal end”, as used herein, refers to the end of the elongated members (or the implantation device or other component on the implantation device) that are nearer the target stenotic opening of the subject during use.

The hollow elongated members may be, for example, a structure of sufficient rigidity to allow the distal end to be pushed through tissue when sufficient force is applied to the proximal end of the device. As such, in some embodiments, the elongated member is not pliant or flexible, at least not to any significant extent. Example materials may include, but are not limited to, metals, metal alloys (e.g., stainless steel), polymers such as hard plastics, etc.

In some embodiments, the hollow elongated member includes a curved tip section at its distal end. The curvature and length of curvature may vary in degree, and may vary according to application, such as with which sinus opening is being accessed, e.g., maxillary sinus, frontal sinus, sphenoid sinus, etc. In some embodiments, to facilitate access to an opening of the maxillary sinus, the curved tip section 604 is configured to bend at an angle ranging from 0° to 90°, such as 10° to 60°, including 20° to 50° from the axis of the non-curved portion of hollow elongated member 601, and the length of the curved tip section is 5 cm or less, such as 3 cm or less, including 2 cm or less. In some cases, to facilitate access to an opening of the frontal sinus, the curved tip section 604 is configured to bend at an angle ranging from 30° to 100°, such as 60° to 100°, including 70° to 95° from the axis of the non-curved portion of hollow elongated member 401, and the length of the curved tip section is 5 cm or less, such as 3 cm or less, including 2 cm or less. In certain embodiments, to facilitate access to an opening of the sphenoid sinus, the curved tip section 604 is configured to bend at an angle ranging from 0° to 90°, such as 0° to 60°, including 0° to 25° from the axis of the non-curved portion of hollow elongated member 601, and the length of the curved tip section is 5 cm or less, such as 4 cm or less, including 2.5 cm or less.

The interior elongated member may be, in some instances, a structure of sufficient rigidity to allow the sinus dilator to be pushed through the stenotic opening when sufficient force is applied to the proximal end of the device, even when the stenotic opening is completely occluded. In some instance, the interior elongated member may be a metal, metal alloy, polymer (hard or pliant and flexible), etc. Further, the interior elongated member is, in some instances, a structure sufficiently pliant and flexible such that the interior elongated member may be relatively displaced in a hollow elongated member having a curved tip section. Example sufficiently pliant and flexible materials may include, but are not limited to, polymers such as plastics, rubber-like polymers, etc. In such cases, the hollow elongated member may provide the rigidity necessary to push the sinus dilator through the stenotic opening with sufficient force applied to the proximal end of the device.

As summarized above, the interior elongated member includes a retention interface adapted to removably couple to the sinus dilator. For example, the retention interface may be configured to mate with (e.g., slide within), clamp on, or removably couple in another way with, the sinus dilator. In some instances, the retention interface is part of the interior elongated member in that the retention interface and interior elongated member are parts of a single unitary piece of material. In other instances, the retention interface may be a separate piece of material that is coupled to the interior elongated member, either removably or non-removably coupled in different embodiments. Retention interfaces that are removably coupled to the interior elongated member may provide the ability to replace retention interfaces (e.g., for sanitation purposes, or replacement purposes) or switch to different types of retention interfaces (e.g., for use with different types or sized sinus dilators).

In some embodiments, the retention interface is adapted to fit within a central passageway of the sinus dilator. The sinus dilator may be, for example, shaped and sized to fit within the contours of the central passage way. The sinus dilator may then be coupled to the retention interface by sliding the sinus dilator onto the retention interface. In some instance, the shape and size of the retention interface matches the contours of the central passageway. Also, in some instances, the interior elongated member may be slid all the way through the central passageway of the sinus dilator with a tip portion extending out of the sinus dilator.

In some aspects, the implantation device is configured to stop the sinus dilator when it is completely slid onto the retention interface so that the dilator cannot continue to slide down the retention interface and interior elongated member. In some instances, the retention interface is shaped to stop the sinus dilator when completely slid on the retention interface, e.g., shaped to include stops. For example, the retention interface may be shaped with a decreasing cross-sectional width closer to the tip. Since the retention interface is shaped and sized to fit with the interior surface of the central passageway of sinus dilator, the retention interface may be adapted to abut a contact surfaces on the sinus dilator, acting as stops for the sinus dilator when completely inserted on the retention interface. Thus, the stops prevent the sinus dilator from being inserted further once the stops are encountered. The stops may provide addition support when force is applied from the proximal end of the device in order to push the sinus dilator through tissue and a stenotic opening. Furthermore, such stops do not inhibit movement of the retention interface in the opposite direction back out the central passageway, to allow for decoupling of the retention interface and the sinus dilator. In some instances, the interior elongated member has a wider cross sectional width than the retention interface such that the wider cross sectional width functions as a stop against a corresponding contacting surface on the sinus dilator. In some instances, the sinus dilator may abut the hollow elongated member when inserted completely on the retention interface. The hollow elongated member may, in such case, function as a stop in place of, or in addition to, any stops provided on the retention interface or interior elongated member.

In some embodiments, the retention interface includes retaining elements that provide an additional securing force to the sinus dilator so that it may not slide back off the retention interface unless a sufficient amount of force is applied to overcome the additional securing force, or until the additional securing force is removed. For example, the retention interface may be adapted to provide an outward force on the central passageway of the sinus dilator, thus providing an outward force on the central passageway which helps retain the sinus dilator coupled to the retention interface. The retention interface may, for instance, include a compressible lip, bump, or other protrusion that is compressed when inserted within the central passageway of the sinus dilator, providing the outward force on the central passageway. Other retaining elements may also be used, e.g., lips, bumps or protrusion that fit within mating recesses on the sinus dilator that "snap" the dilator onto the retention interface. In some instances, the distal tip of the retention interface is split (e.g., in a polymer flexure design), with each arm of the split tip stressed or flexed inward towards one another when inserted within the central passage way of the sinus dilator. In such case, for example, the arms of the split tip have a tendency to return to their unstressed or not flexed position, thus providing the outward force to the interior of the central passageway of the sinus dilator.

Sufficient force to overcome the additional securing force by the retaining elements may be provided by, for example, withdrawing the interior elongated member while the sinus dilator is securely fit within the stenotic opening. As another example, the sufficient force may be provided by the hollow elongated member being displaced and pushed into the sinus dilator to push the sinus dilator off the retention interface.

Additionally, the distal tip of the retention interface, whether split or not, may include a small lip, bump, or other protrusion that functions as a retaining element to provide the additional securing force necessary to resist the sinus dilator from moving back off the retention interface. It should be appreciated that the size and shape of the protrusions will determine the amount of sufficient force necessary to overcome the additional securing force provided by the protrusions.

It should also be appreciated that the above described retaining elements are exemplary and that other types of retaining elements may be implemented. It should also be appreciated that the retaining element described above, and equivalents thereof, serve as means for providing an additional securing force to the sinus dilator when inserted on the retention interface.

In some embodiments, the implantation device may include a lumen that extends to the distal end of the implantation device. For example, the lumen may extend within the interior elongated member and include an opening at the distal tip of the elongated member. It should be appreciated that the lumen may, in some instances, be formed by the interior elongated member or formed by a tube positioned within the interior elongated member. In alternative embodiments, the lumen may be positioned within the hollow elongated member but not within the interior elongated member.

In some instances, implantation device is configured to couple the lumen to a fluid source to dispense fluid into the sinus cavity or nasal cavity before, during or after placement of the sinus dilator 300 in the stenotic opening. The term "fluid" is used herein generally to refer to any variety of fluids, mists, gels, single or multi-phase liquid, etc., or combinations thereof. The fluid source may be located in various positions, depending on design, e.g., being located on or in the device, attaching to the device (e.g., a cartridge, etc.), or coupling to the device via a connection port, etc. In some instances, the lumen is coupled to a hollow tube in the handheld member that brings the lumen in fluid communication with the fluid source. Example fluids that may be dispensed are, for example, fluids comprising water, saline solution, drugs, etc. Example drugs that may be present in the fluid (e.g., in fluid or solid form) may include, but are not limited to fluids comprising one or more analgesics, anesthetics, anti-inflammatories, antibiotics, steroids, drugs that control or limit bleeding (e.g., vasoconstrictors), etc.). Vasoconstrictors may include, for example, oxymetazoline, epinephrine, tranexamic acid, salts thereof, combinations thereof, and the like.

In some embodiments, the lumen may be coupled to a pellet source or other source of solid, such as powder, etc. In such case, the lumen is used to dispense solid pellets, for example, into the sinus cavity and/or nasal cavity before, during or after placement of the sinus dilator 300 in the stenotic opening. Furthermore, in some instances, the lumen may be coupled to a suction source (e.g., vacuum source) in order to provide suctioning, in order to remove fluid, tissue debris, etc. It should be appreciated that in some instances more than one lumen may be implemented. For example, in some instances, one lumen may be provided to dispense fluids while another lumen is provided for suctioning purposes.

In some embodiments, the implantation device may be configured to include a camera positioned near the distal end of the hollow elongated member in order to assist in visualizing the stenotic site, nasal cavity, or sinus cavity. In some instances, the camera may be positioned on the exterior surface of the hollow elongated member and, for example, electrically coupled to a monitor via an electrical wire extending along or within the hollow elongated member. In other instances, the camera may be positioned within the hollow elongated member. For example, a camera may be inserted at the tip of the interior elongated member and electrically coupled to a monitor via an electrical wire extending within the interior elongated member.

The implantation devices, or components thereof, may be configured for one time use (i.e., disposable) or re-usable, e.g., where the components are configured to be used two or more times before disposal, e.g., where the device components are sterilizable.

Figure 3:
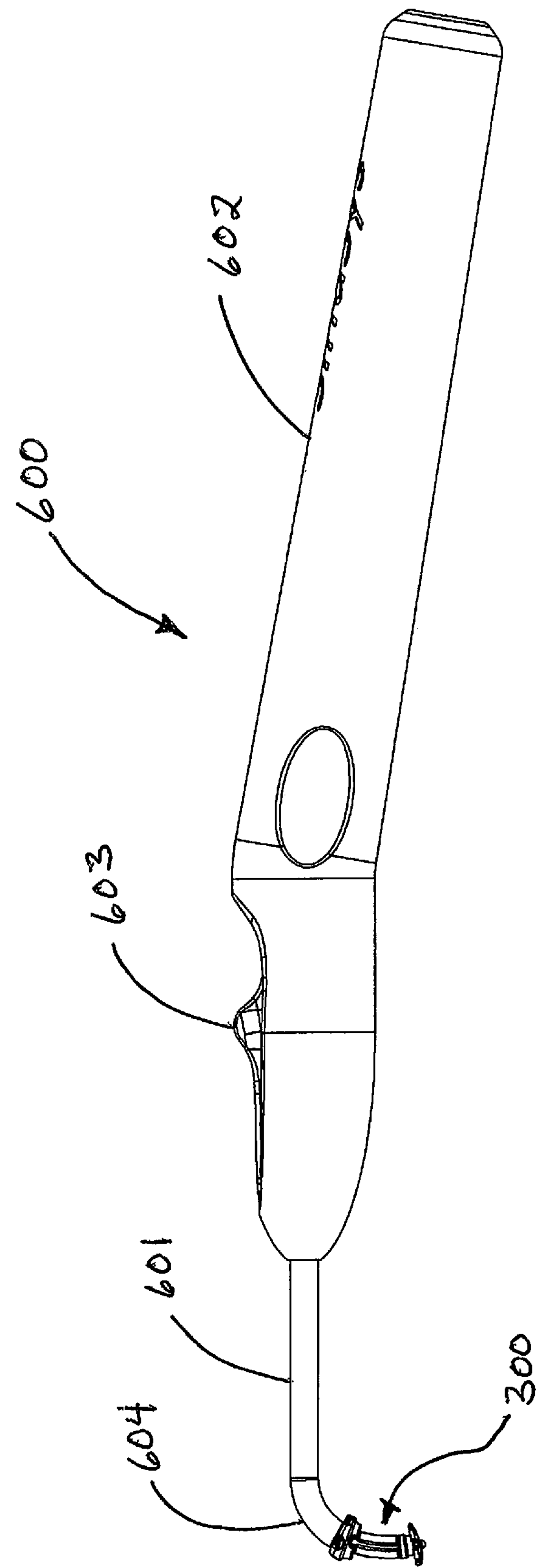
FIG. 3 illustrates a side view of an implantation device 600 with a sinus dilator 300 coupled therewith, according to some embodiments.

FIG. 3 illustrates a side view of an implantation device 600 with a sinus dilator 300 coupled therewith, according to some embodiments. Implantation device 600 is shown comprising a handheld member 602 coupled to the proximal end of a hollow elongated member 601. Implantation device 600 has a handheld member 602 sized to be gripped by a physician's hand with trigger 603 adapted to be actuated by the physician's thumb. At the distal end of the hollow elongated member 601 (e.g., cannula), sinus dilator 300 is coupled to a retention interface (not shown) on an interior elongated member (not shown in FIG. 3 but shown in FIG. 4) extending within the hollow elongated member 601. The sinus dilator 300 abuts the distal end of the hollow elongated member 601. The hollow elongated member 601 has a curved tip section 604. The dimensions and tip curvature of the hollow elongated member 601 shown in FIG. 3 may vary to facilitate implantation of the sinus dilator into specific paranasal sinuses, such as frontal sinus, a sphenoid sinus or a maxillary sinus.

Figure 4:
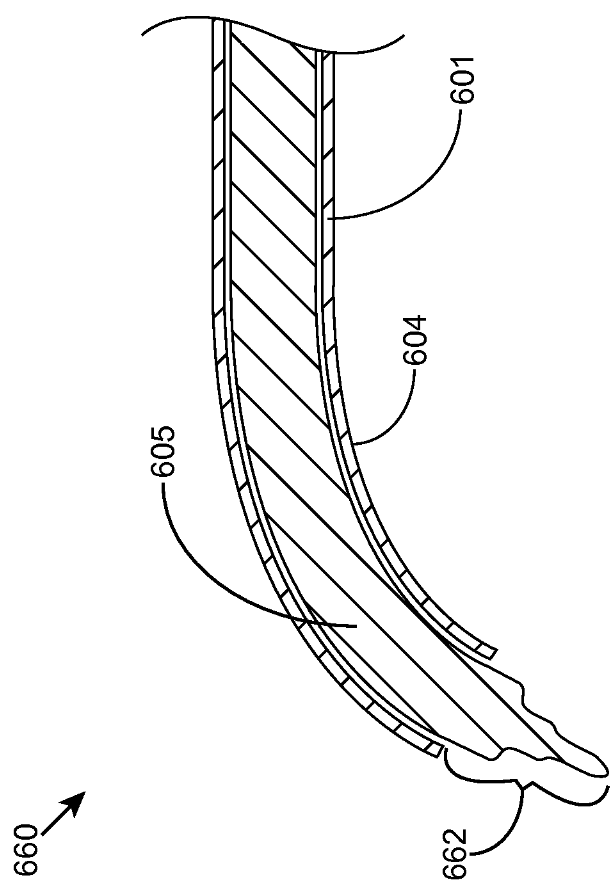
FIG. 4 illustrates a cross-sectional side view of the distal end of the implantation device 600 in FIG. 2 without a sinus dilator coupled thereto, according to some embodiments.

FIG. 4 illustrates a cross-sectional side view of the distal end of the implantation device 600 in FIG. 4 without a sinus dilator coupled thereto, according to some embodiments. Distal end 660 of implantation device 600 is shown including a curved tip section 604 of hollow elongated member 601. Interior elongated member 605 is shown extending within hollow elongated member 601 and curved tip section 604. Interior elongated member 605 includes a retention interface 662 that extends outside the hollow elongated member 601 and couples to the sinus dilator. The retention interface, shown in this embodiment, is shaped and sized to fit within the central passage way of a sinus dilator.

Figure 5:
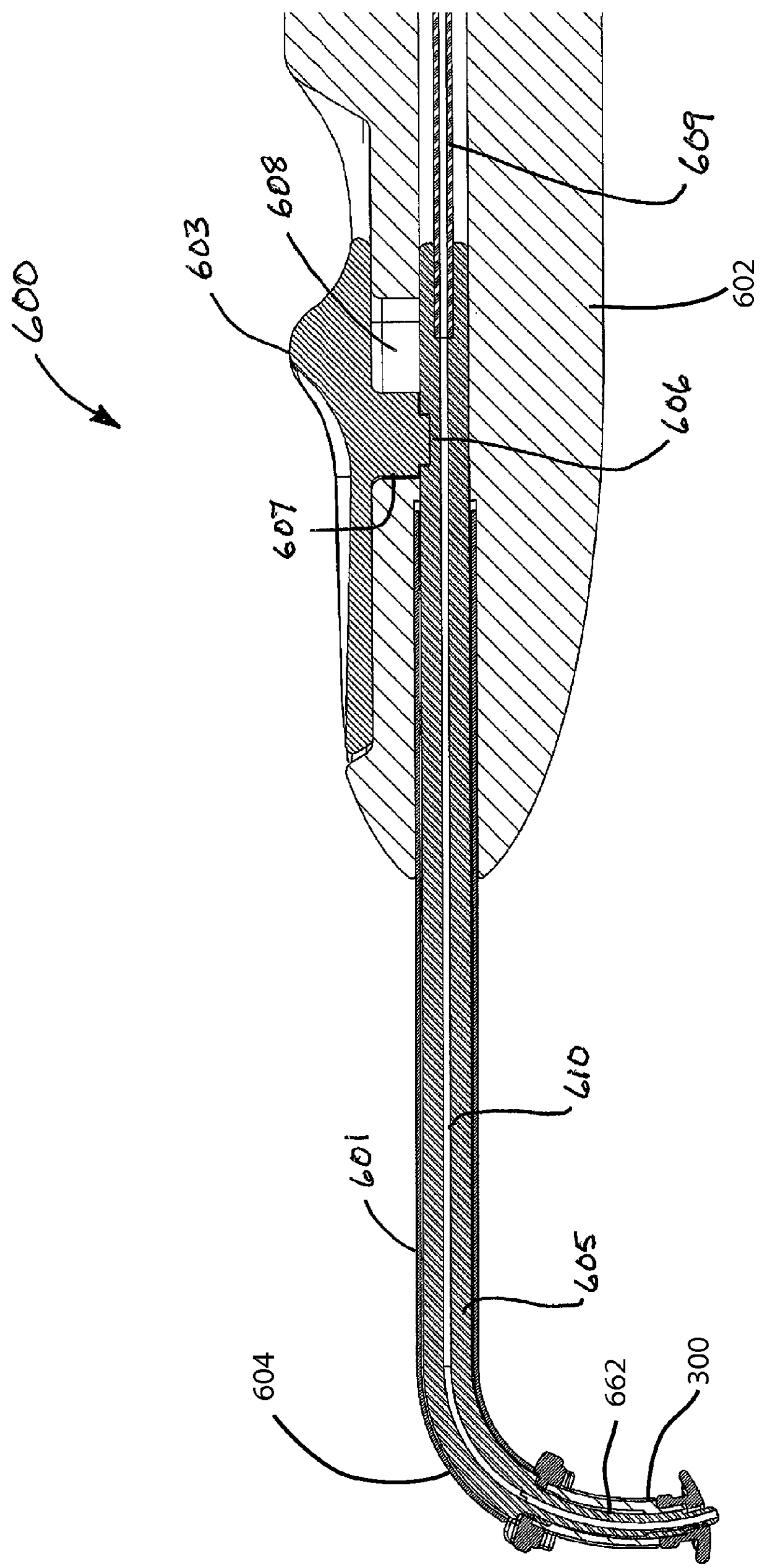
FIG. 5 illustrates a cross sectional side view of the distal end of an implantation device prior to positioning the sinus dilator within the stenotic opening, according to some embodiments.

FIG. 5 illustrates a cross sectional side view of the distal end of an implantation device prior to positioning the sinus dilator within the stenotic opening, according to some embodiments. Implantation device 600 has a handheld member 602 coupled to the proximal end of a hollow elongated member 601. At the distal end of the hollow elongated member 601 (e.g., cannula), sinus dilator 300 is coupled to a retention interface 662 on an interior elongated member 605 (e.g., a flexible rod) that is slidably positioned within the hollow elongated member 601. The sinus dilator 300 abuts the distal end of the hollow elongated member 601. The hollow elongated member 601 has a curved tip section 604. The dimensions and tip curvature of the hollow elongated member 601 shown in FIG. 3 may be suited for implanting the sinus dilator 300 into a maxillary sinus opening, for example.

Interior elongated member 605 is further shown to include an optional lumen 610. In some instances, lumen 610 is in fluid communication with hollow tube 609. Tube 609 can be connected to a fluid source (e.g., water, saline and/or drug solution) or solid pellet source, which enables fluid or solid pellets to be injected into the sinus cavity and/or nasal cavity via the lumen before, during or after placement of the sinus dilator 300 in the stenotic opening. Furthermore, in some instances, tube 609 can be connected to a vacuum source in order to provide suctioning.

In the embodiment shown in FIG. 5, interior elongated member 605 is coupled to trigger 603 such that actuation of trigger 603 causes the interior elongated member 605 to displace proximally within the hollow elongated member 601. Trigger 603 and interior elongated member 605 are coupled via a trigger arm 607 on the trigger that engages and fits within a notch 606 on the interior elongated member. Trigger arm 607 moves within a slot 608 in handheld member 602. Trigger 603 is biased, e.g., using a spring or other biasing means (not shown), toward the position shown in FIG. 5 with the end of interior elongated member 605 extending out from the end of curved tip section 604. When in this position, the sinus dilator 300 may be slid onto the retention interface of interior elongated member 605, as shown in FIG. 5.

Figure 6:
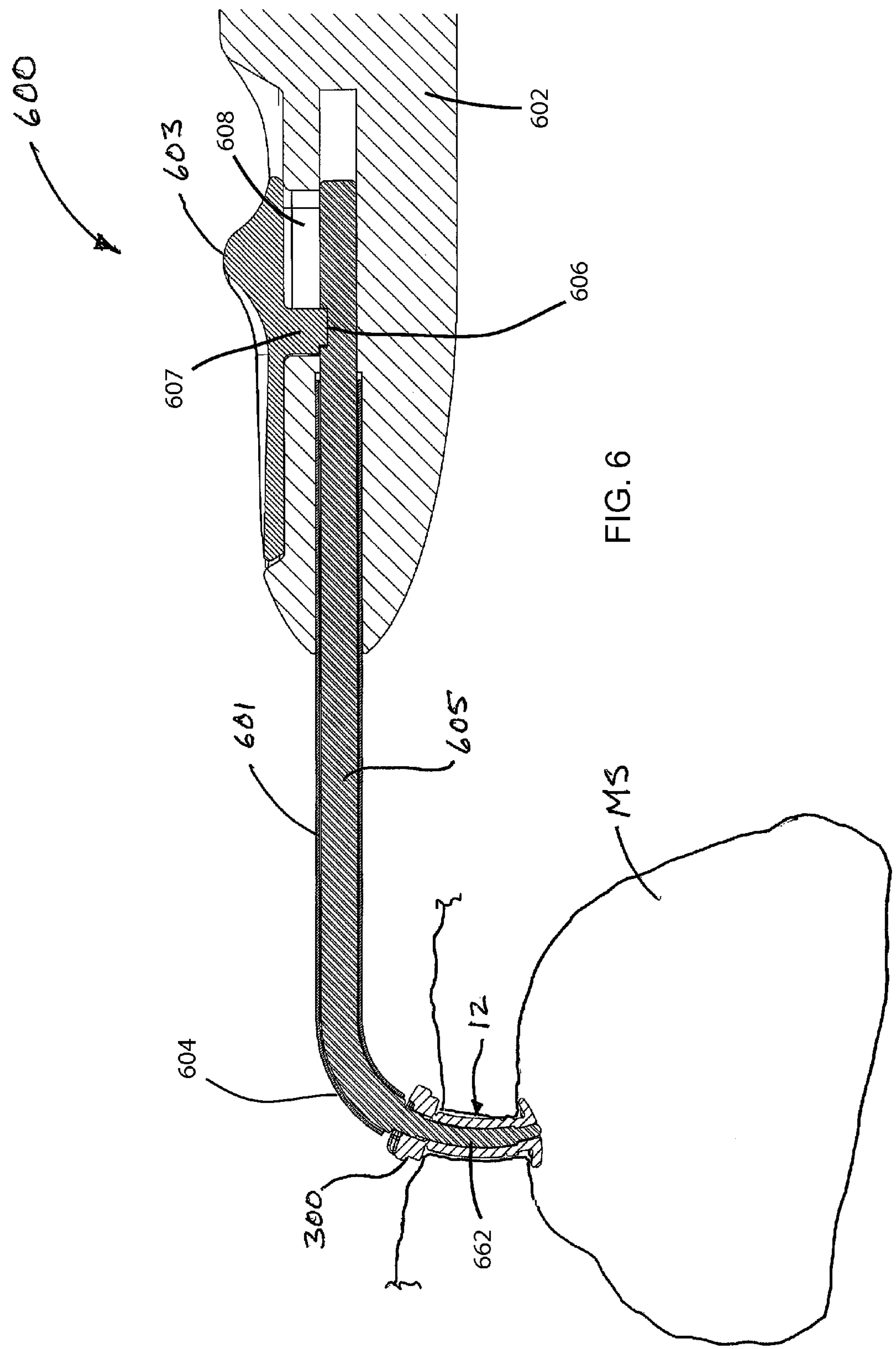
FIG. 6 illustrates a cross sectional side view of the distal end of an implantation device when the sinus dilator is positioned within the stenotic opening, according to some embodiments.

In this configuration, the implanter 600 is ready for positioning and implanting the sinus dilator 300. The user (e.g., physician) then introduces the hollow elongated member 601 and sinus dilator 300 through the patient's nasal cavity to reach the stenotic opening 12 of a sinus (which may be occluded), such as a maxillary sinus (MS). The physician then positions the sinus dilator into the stenotic opening 12, as shown in FIG. 6. FIG. 6 illustrates a cross sectional side view of the distal end of an implantation device when the sinus dilator is positioned within the stenotic opening 12, according to some embodiments. It should be appreciated that the description for the embodiment shown in FIG. 6 is the same for the embodiment in FIG. 5, except that the embodiment shown in FIG. 6 does not include the lumen in FIG. 5.

Figure 7:
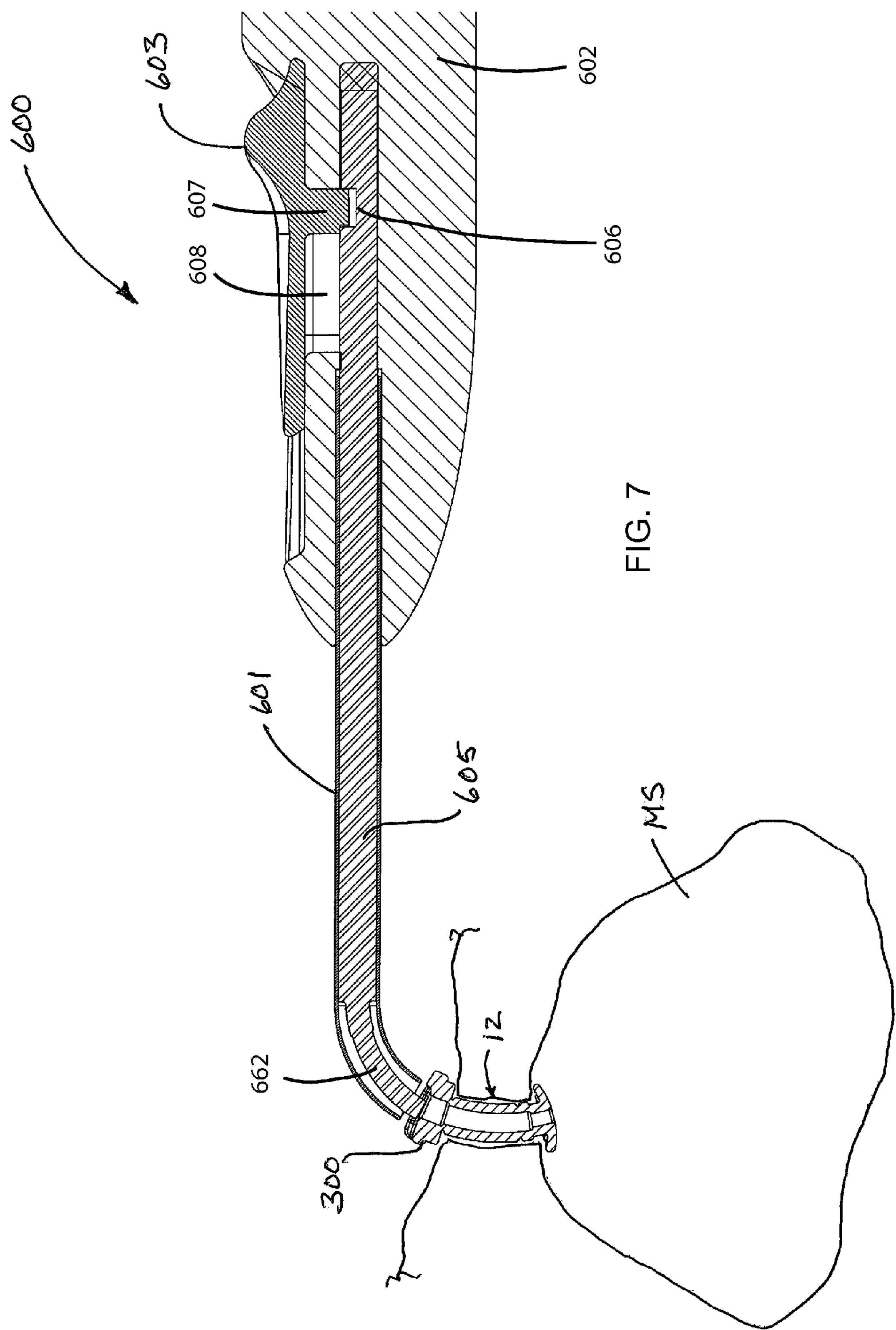
FIG. 7 illustrates a cross-sectional side view of the distal end the implantation device of FIG. 4, after the retention interface is decoupled from the sinus dilator.

Once the sinus dilator 300 is positioned within the opening 12, the trigger 603 is activated, releasing the sinus dilator 300. FIG. 7 illustrates a cross-sectional side view of the distal end of the implantation device of FIG. 6, after the retention interface 662 is decoupled from the sinus dilator 300. In the embodiment shown, this occurs by means of displacing (e.g., sliding) the trigger 603 in a proximal direction to the position shown in FIG. 6 while the hollow elongated member 601 remains in a relatively fixed position to the handheld member 602. The retraction of at least a portion of the retention interface 662 within the hollow elongated member 601 causes the interior elongated member 605 to withdraw out of the sinus dilator 300, as shown in FIG. 6. Thereafter, the physician may remove the hollow elongated member 601 back out of the nasal cavity.

In some aspects of the present disclosure, the implantation device is configured to stop the sinus dilator when it is completely slid onto the retention interface so that the dilator cannot continue to slide down the retention interface and interior elongated member. In some instances, the retention interface is shaped to stop the sinus dilator when completely slid on the retention interface, e.g., shaped to include stops. For example, the retention interface may be shaped with a decreasing cross-sectional width closer to the tip.

Figure 8:
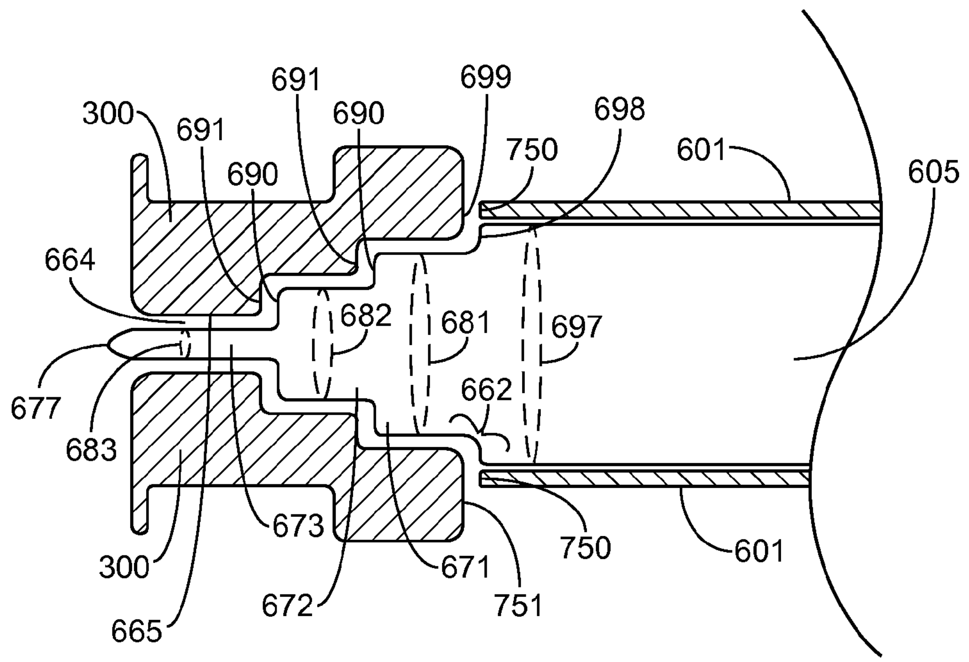
FIG. 8 illustrates a cross sectional side view of a retention interface that is shaped with a decreasing cross-sectional width closer to the tip, according to some embodiments.
Figure 9:
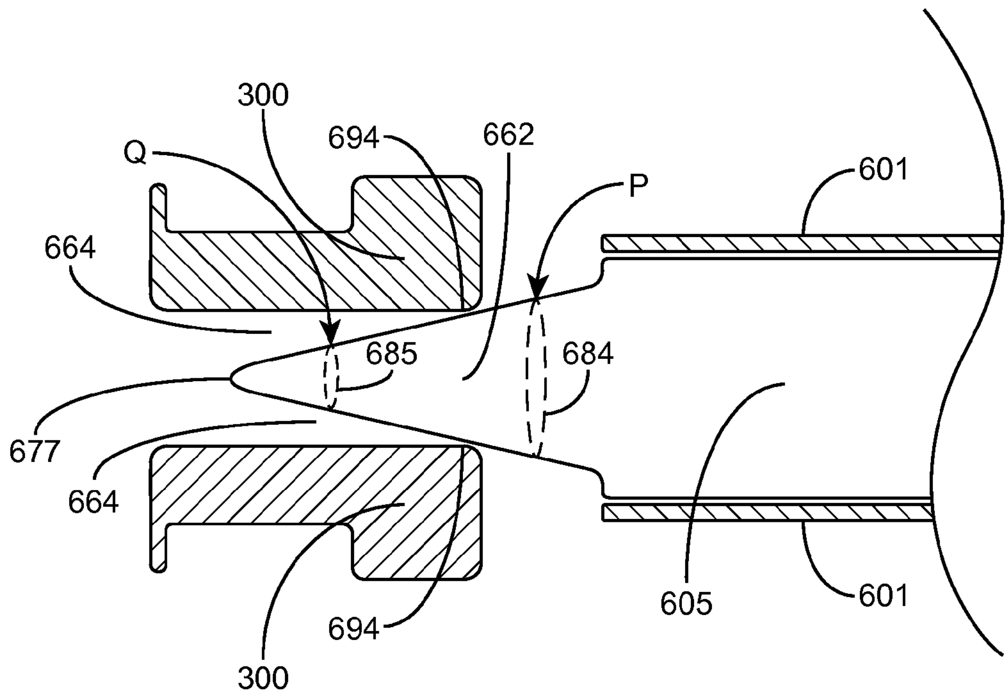
FIG. 9 illustrates a cross sectional side view of a retention interface that is shaped with a decreasing cross-sectional width closer to the tip, according to some embodiments.

FIGS. 8 and 9 illustrate a cross sectional side view of a retention interface that is shaped with a decreasing cross-sectional width closer to the tip, according to some embodiments. As shown, interior elongated member 605 is positioned within hollow elongated member 601 and includes retention interface 662 that is inserted into a central passageway 664 of sinus dilator 300.

In FIG. 8, retention interface 662 is shown as a portion of the interior elongated member that is shaped to comprise three cylindrical sections 671, 672, 673 with decreasing diameters closer to the distal tip 677 of the retention interface 662. The retention interface 662 is positioned outside the hollow elongated member 601 and has a decreasing cross-sectional width closer to the tip. As shown, cross sectional width 683 of the cylindrical section 673 is smaller than cross sectional width 682 of the cylindrical section 672, which is smaller than cross sectional width 681 of the cylindrical section 671. It should be appreciated that the following embodiment is exemplary and that other number of cylindrical sections (e.g., one, two, three, four, etc.) may be implemented, and further, that other shapes both regular and irregular may be implemented in place of, or in addition to cylindrical shapes.

Since the retention interface 662 is shaped and sized to fit with the interior surface 665 of the central passageway 664 of sinus dilator 300, portions of the retention interface 662 (e.g., at points where the cross-sectional width is large enough to abut the sinus dilator) function as stops 690 that abut contact surfaces 691 when sinus dilator 300 is completely inserted on the retention interface 662. Thus, stops 690 prevent the sinus dilator 300 from being inserted further once the stops 690 are abutted. The stops 690 may provide addition support when force is applied from the proximal end of the device in order to push the sinus dilator 300 through tissue and stenotic opening. Furthermore, the stops 690 shown do not inhibit movement of the retention interface in the opposite direction back out the central passageway, allowing decoupling of the retention interface and sinus dilator. In some instances, such as shown in FIG. 8, the interior elongated member 605 has a wider cross sectional width 697 than the retention interface 662 such that a section 698 of the interior elongated member 605 having the wider cross sectional width 697 functions as a stop against a corresponding contacting surface 699 on the sinus dilator.

In some embodiments, the sinus dilator 300 may abut the hollow elongated member 601 when inserted completely on the retention interface 662. The distal tip of the hollow elongated member 601 may, in such case, function as a stop in place of, or in addition to, any stops provided on the retention interface 662 or interior elongated member 605. For example, as shown in FIG. 8, the distal tip 750 of the hollow elongated member 601 abuts contacting surfaces 699 and 751 on sinus dilator 300 and functions as a stop in addition to the other stops provided on the retention interface 662 or interior elongated member 605. Distal tip 750 contacts contacting surfaces 699 and 751 on the sinus dilator.

In FIG. 9, retention interface 662 is shown as a portion of the interior elongated member 605 that is cone shaped with a decreasing cross-sectional diameter closer to the distal tip 677 of the retention interface 662. The retention interface 662 is positioned outside the hollow elongated member 601 and has a continuously decreasing cross-sectional width closer to the tip 677. As shown, cross sectional width 685 at point Q of the conical retention interface 662 is smaller than cross sectional width 684 at point P of the conical retention interface 662. The cross sectional width that is approximately the same width as the cross-sectional width of the central passageway will abut a contact surface on the central passageway and functions as a stop for the sinus dilator when completely inserted on the retention interface. For example, the portion of the retention interface 662 having cross section width 684 functions as a stop and abuts contacting surfaces 694 on sinus dilator 300. As stated above, the sinus dilator 300 cannot be inserted further once the stop is encountered. Further, the stop may permit force to be applied from the proximal end of the device 600 (see e.e, FIG. 3) in order to push the sinus dilator 300 through tissue and the stenotic opening 12 (see e.g., FIG. 6), but does not inhibit movement of the retention interface 662 in the opposite direction back out the central passageway 664.

Figure 10:
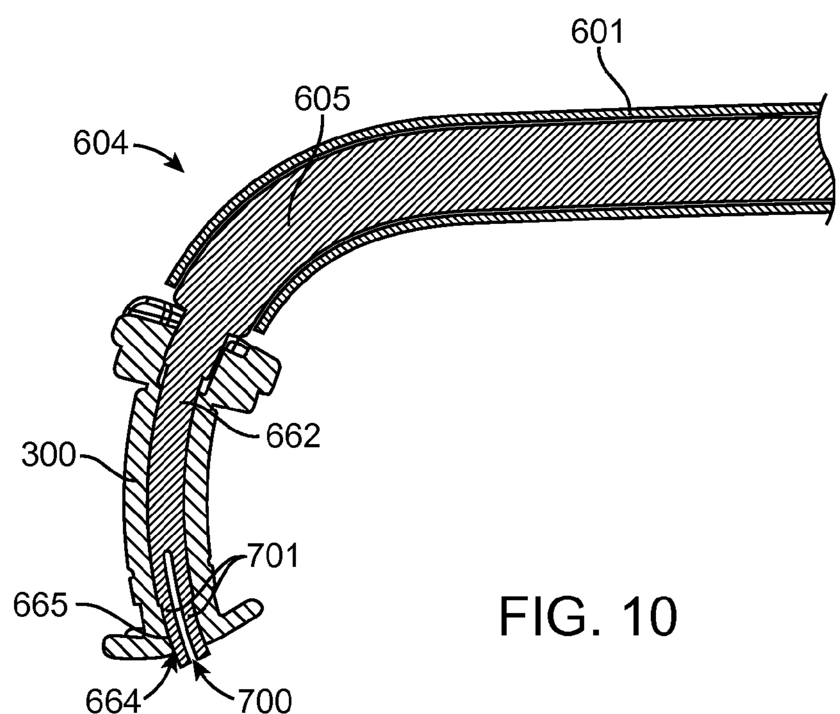
FIG. 10 illustrates a side cross-sectional view of a portion of an implantation device having a retention interface including a split distal tip, according to some embodiments.

In some embodiments, the retention interface includes retaining elements that provide an additional securing force to the sinus dilator so that it may not slide back off the retention interface unless a sufficient amount of force is applied to overcome the additional securing force, or until the additional securing force is removed. FIG. 10 illustrates a side cross-sectional view of a portion of an implantation device having a retention interface 662 including a split distal tip 700, according to some embodiments. As shown, interior elongated member 605 comprises retention interface 662 and positioned within hollow elongated member 601 with the retention interface 662 outside the hollow elongated member 601. The split distal tip 700 is shown comprising arms 701 that are stressed inward by the central passageway 664 when inserted into the sinus dilator 300, thus providing an outward force upon the interior surface 665 of the central passageway 664. The outward force serves as an additional securing force by providing frictional force between the retention interface 662 and the sinus dilator 300, thus inhibiting displacement of the sinus dilator back off the retention interface until sufficient force is applied to overcome it.

Figure 11:
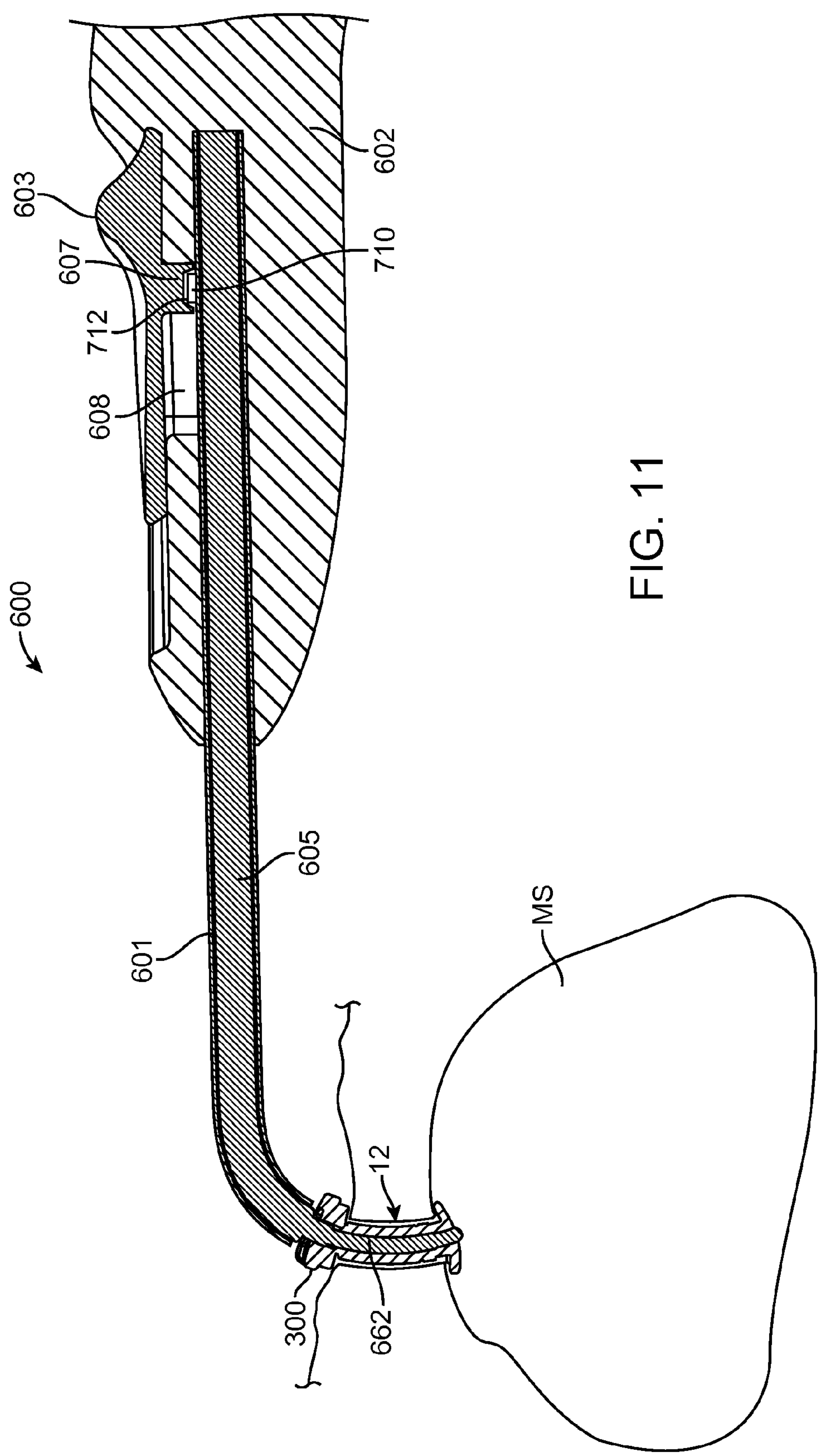
FIG. 11 illustrates a cross sectional view of the distal end of an implantation device when the sinus dilator is positioned within the stenotic opening, according to some embodiments.
Figure 12:
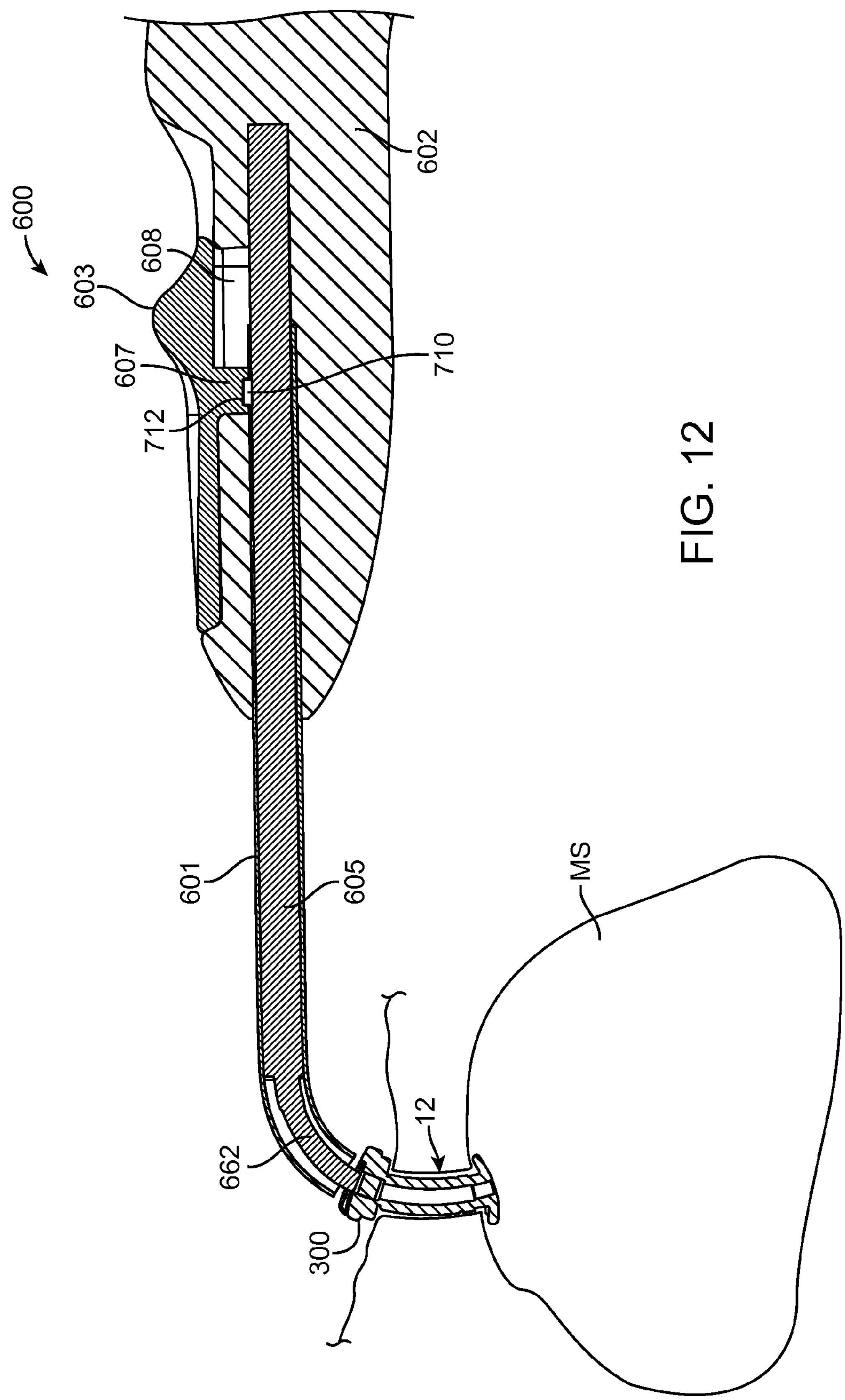
FIG. 12 illustrates a cross-sectional view of the distal end the implantation device of FIG. 9, after the retention interface is retracted and decoupled from the sinus dilator, according to some embodiments.

In some embodiments, the relative displacement of the interior elongated member with respect to the hollow elongated member may comprise distally displacing the hollow elongated member away from the handheld member while the retention interface remains in a relatively fixed position to the handheld member. FIGS. 11 and 12 illustrate a cross sectional view of the distal end of an implantation device before and after the trigger is actuated, respectively, according to some embodiments. Implantation device 600 has a handheld member 602 coupled to the proximal end of a hollow elongated member 601. At the distal end of the hollow elongated member 601 (e.g., cannula), sinus dilator 300 is coupled to a retention interface 662 on an interior elongated member 605 (e.g., a flexible rod) is slidably positioned within the hollow elongated member 601. The sinus dilator 300 abuts the distal end of the hollow elongated member 601. The hollow elongated member 601 has a curved tip section 604. The dimensions and tip curvature of the hollow elongated member 601 shown in FIGS. 11 and 12 may be suited for implanting the sinus dilator 300 into a maxillary sinus opening, for example.

In the embodiment shown, hollow elongated member 601 is coupled to the trigger 603 such that actuation of the trigger 603 causes the hollow elongated member 601 to be relatively displaced with respect to the interior elongated member 605. More specifically, the hollow elongated member 601 is distally displaced away from the handheld member 602 while the interior elongated member 605 remains in a relatively fixed position with respect to the handheld member 602. Trigger 603 and hollow elongated member 601 are shown coupled via a coupling mechanism comprising a protrusion 710 on the hollow elongated member 601 that engages and fits with a notch 712 on a trigger arm 607 on the trigger 603. Trigger arm 607 moves within a slot 608 in handheld member. Trigger 603 is biased (e.g., using a spring or other biasing means) toward the position shown in FIG. 11 with the end of interior elongated member 605 extending out from the end of curved tip section 604. When in this position, the sinus dilator 300 may be slid onto the retention interface of interior elongated member 605, as shown in FIG. 11.

In this configuration, the implanter 600 is ready for positioning and implanting the sinus dilator 300. The physician then introduces the hollow elongated member 601 and sinus dilator 300 through the patient's nasal cavity to reach the stenotic opening 12 of a sinus (which may be occluded), such as a maxillary sinus (MS), as shown. The physician then positions the sinus dilator 300 into the stenotic opening.

FIG. 11 illustrates a cross sectional view of the distal end of an implantation device 600 when the sinus dilator 300 is positioned within the stenotic opening, according to some embodiments.

Once the sinus dilator 300 is positioned within the stenotic opening 12, the trigger 603 is activated, releasing the sinus dilator 300. FIG. 12 illustrates a cross-sectional view of the distal end the implantation device of FIG. 11, after the retention interface is retracted and decoupled from the sinus dilator, according to some embodiments. In the embodiment shown, this occurs by means of sliding the trigger 603 in a distal direction to the position shown in FIG. 12, which causes the hollow elongated member 605 to displace away from the handheld member 602 and push the sinus device 300 off of the retention interface 662 as the interior elongated member 601 remains in a relatively fixed position to the handheld member 602, as shown in FIG. 12. Thereafter, the physician may remove the hollow elongated member 601 back out of the nasal cavity.

Figure 24:
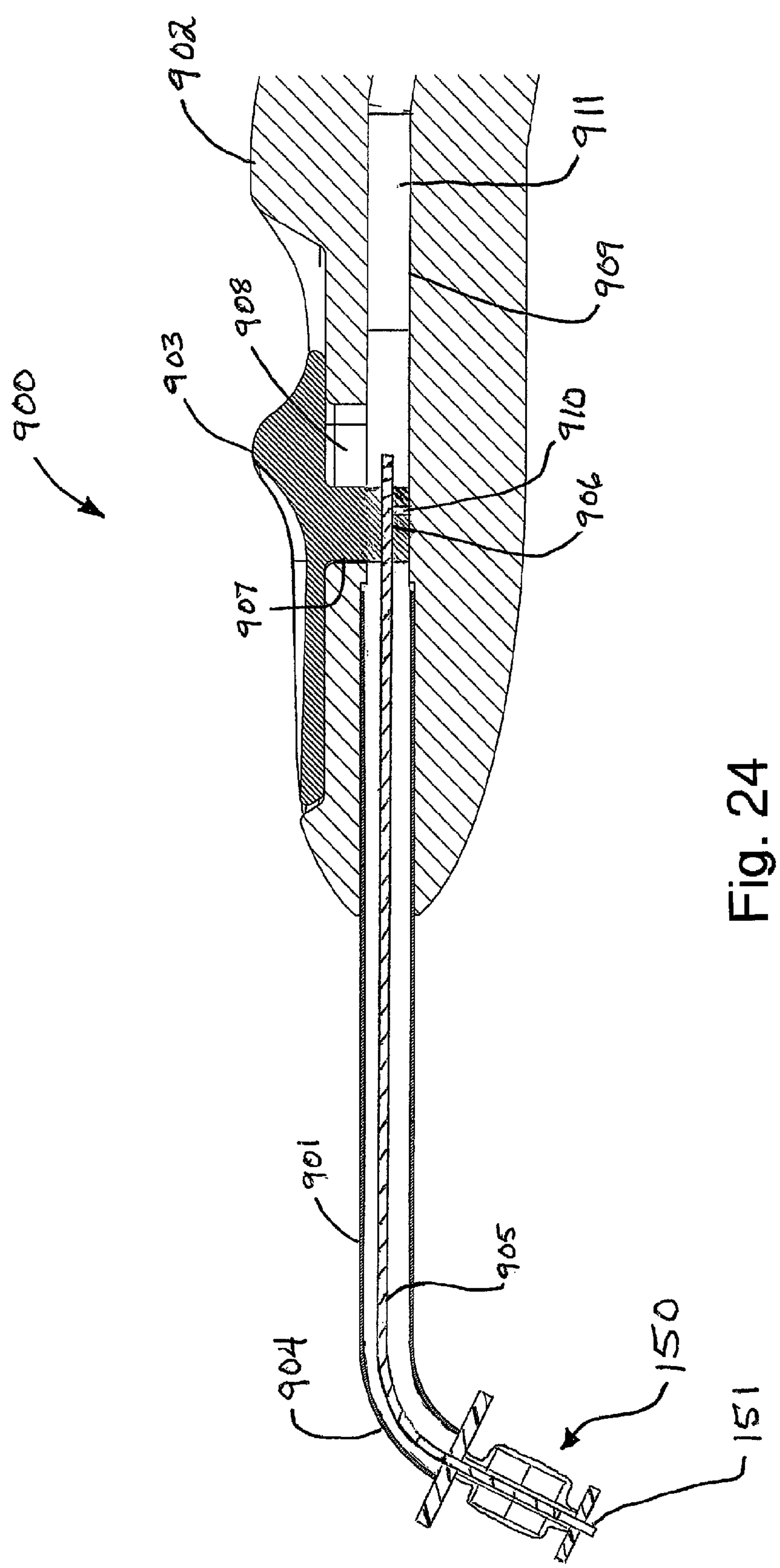
FIG. 24 is a cross sectional view of a device for inserting an expandable device into a paranasal sinus opening, according to embodiments of the present disclosure.

Another embodiment of an osmotic dilator insertion device 900 is shown in FIG. 24. Similar to device 600 shown in FIGS. 11 and 12, device 900 also has a handle 902 with a hollow internal lumen 909, an elongated hollow member 901 mounted on the handle 902 within lumen 909, the member 901 having a curved distal tip section 904, and a slidable trigger 903 with trigger arm 907 which moves back and forth within slot 908. A wire 905 is slidably positioned within member 901. The wire 905 can be for example made from stainless steel having a diameter of about 0.3 mm to 0.6 mm. The wire 905 has a curved distal tip which facilitates advancing and retracting the wire 905 through the curved tip section 904 of hollow elongated member 901. The proximal end of wire 905 is attached to trigger arm 907 by means of the proximal end of the wire 905 extending into passageway 906 and then being secured therein using a set screw 910. With the trigger 903 in the advanced position (i.e., the left-most position as shown in FIG. 24), the distal end of wire 905 extends out from the distal open end of member 901 and provides a length of wire that is sufficient to mount osmotic dilator 150 thereon. In some instances, the length of wire 905 extending beyond the end of member 901 is such that the wire 905 extends through one third or more of the length of the internal tube 151 of dilator 150. In certain cases, tube 151 has a straight axis and the axis of the distal end of wire 905 is curved, such that sufficient friction is created to keep osmotic dilator 150 securely mounted on the distal end of the wire 905 during placement within a sinus ostium. Alternatively, the wire 905 can extend completely through and beyond the distal end of tube 151 and be used by the surgeon to pierce a small hole through a stenotic ostium just prior to dilator 150 insertion. Optionally, the distal end of member 901 can be fitted with a slotted flange (not shown in FIG. 24) that engages the proximal anchor of dilator 150 and keeps the dilator 150 from rotating around wire 905 during insertion of the dilator 150 into a sinus ostium.

In certain embodiments, device 900 includes a light source 911 which in some instances is a directional light source, such as a low energy laser. The light source 911 emits light into the lumen of hollow member 901. When the light source 911 is positioned as shown in FIG. 24, the trigger arm 907 may be off set with respect to the position of light source 911 to allow the light to reach the lumen of member 901, or the arm 907 may be constructed of a light-transmitting material such as clear plastic or glass. In some embodiments, in order to allow the light to "bend" around the curved tip 904, the interior surfaces of member 901 can be highly polished (e.g., in the case of member 901 being made of a metal such as stainless steel) or otherwise provided with a mirrored surface treatment. In certain cases, at least portions of the dilator 150 (e.g., the proximal anchor or expandable membrane) are constructed of light transmitting and/or translucent materials so that the light from the light source 911 causes at least portions of the dilator 150 to become illuminated. The illumination may have sufficient intensity so that the emitted light can be seen through the patient's facial tissue. The position of the illuminated dilator 150 may help the physician to correctly position the dilator in the ostium. As an alternative to the light source 911, the osmotic dilator 150 described herein may be placed using an illuminated guide wire, for example of the type described in Goldfarb et al. (U.S. Pat. No. 7,559,925), that extends through the elongated hollow members 601 and/or 901 and optionally through the internal lumen of the osmotic dilator 150.

Sinus Dilators

Provided below are paragraphs describing example sinus dilators that may be implanted with the implantation device described in the present disclosure. It should be appreciated that the described embodiments of sinus dilators presented herein are exemplary, and that the implantation device may be implemented with other sinus dilators. Further details and examples of sinus dilators are disclosed in U.S. Provisional Application Nos. 61/378,360 filed Aug. 30, 2010, and 61/416,248 filed Nov. 22, 2010, and in a U.S. Non-provisional application filed concurrently with the present application and entitled, "DEVICES AND METHODS FOR DILATING A PARANASAL SINUS OPENING AND FOR TREATING SINUSITIS", the entire disclosures of which are herein incorporated by reference.

According to some embodiments, the sinus dilators include an expandable driver. In certain embodiments, the driver is configured to expand from a non-expanded configuration to an expanded configuration. For instance, the driver may be configured to expand in volume from a non-expanded configuration to an expanded configuration. The non-expanded configuration of the sinus dilators may be sized to be positioned within the stenotic opening by an implantation device as described herein. When implanted, the driver is configured to expand in size to an expanded configuration, where the expanded configuration dilates the stenotic opening.

In certain embodiments, the driver is configured to be a self-expanding driver. By "self-expanding" is meant that the driver may expand from the non-expanded configuration to the expanded configuration without external intervention from a user or a health care practitioner. For example, the self-expanding driver may be self-contained, such that the driver is configured to expand without connection to an external pressure source. As such, self-expanding drivers as described herein function without the need for an external pressure source or a pressure monitoring device. In some cases, the self-expanding driver expands from the non-expanded configuration to the expanded configuration upon absorbing fluid from the surrounding environment when the device is in use. For instance, the self-expanding driver may expand from the non-expanded configuration to the expanded configuration upon absorbing water from the surrounding tissues of the stenotic opening when the device is in use. Self-expanding drivers may be configured to expand the expandable portion of the device by various ways, such as, but not limited to, an osmotic agent, a swellable agent (e.g., a swellable polymer), combinations thereof, and the like.

In certain embodiments, the driver includes a swellable agent. In some cases, the swellable agent may be configured to expand upon adsorption of fluid from the surrounding tissues after insertion of the device into the stenotic opening of the subject. For example, the swellable agent may be configured to absorb water from the surrounding tissues and expand.

In certain embodiments, the driver includes an osmotic agent. As used herein, the terms "osmotic agent," "osmotically active agent" and "osmoagent" are used interchangeably and refer to an agent that facilitates the diffusion of water from a region of high water potential (e.g., low solute concentration) through a semipermeable membrane to a region of low water potential (e.g., high solute concentration) until a state of dynamic equilibrium is reached. In some instances, the osmotically active agent may be configured to absorb water flowing through a semipermeable membrane from the surrounding tissues after insertion of the device into the stenotic opening of the subject and expand. In certain embodiments, the osmotic agent and semipermeable membrane are configured to have approximately a zero order rate of expansion.

Embodiments of the presently disclosed devices include an expandable portion. The expandable portion is configured to expand from a non-expanded configuration to an expanded configuration. In certain embodiments, the expandable portion is configured to expand in size from a non-expanded configuration to an expanded configuration. The expandable portion may be configured to expand in size without significantly increasing in volume, such as by stretching in one or more dimensions from the non-expanded configuration. The expandable portion may be positioned peripherally around the driver. For instance, the expandable portion may be disposed on an exterior surface of the driver. In these embodiments, expansion of the underlying driver expands the expandable portion from its non-expanded configuration to its expanded configuration.

Aspects of the present disclosure include devices that have an expandable portion, where the expandable portion includes a membrane. The membrane may be an elastic membrane, such that the membrane is configured to expand from the non-expanded configuration to the expanded configuration, as described herein. In certain instances, the membrane is a semipermeable membrane. By "semipermeable" is meant a membrane that is permeable to solvent but not significantly permeable to solute across a concentration gradient, such as a membrane that allows solvent (e.g., water) molecules to pass through the membrane by osmosis from a region of low solute concentration to a region of high solute concentration until a state of dynamic equilibrium is reached. For instance, a semipermeable membrane may be configured to allow water to pass through the membrane by osmosis from a region of low solute concentration (e.g., high water potential) to a region of high solute concentration (e.g., low water potential) until a state of dynamic equilibrium is reached.

In certain embodiments, the sinus dilator includes a conduit (e.g., central passageway) that defines an interior lumen of the device. The conduit includes a distal end configured to be in fluid communication with an interior lumen of the paranasal sinus in the subject. As used herein, the term "distal" refers to the end of the device that is inserted into a paranasal sinus opening of the subject during use. The conduit also includes a proximal end configured to be in fluid communication with a nasal cavity in the subject. As used herein, the term "proximal" refers to the end of the device that remains on the nasal cavity side of the stenotic opening when the device is positioned in the stenotic opening during use.

In some embodiments, the implantation device is configured to couple to the sinus dilator by a retention interface, such as described herein, that slides within the conduit of the implantation device. In some instances, the retention interface is shaped and sized to fit within the conduit. In some instances, the shape of the retention interface matches the contour of the conduit. The retention interface, in some instance, may be configured to extend all the way through the conduit with a portion of the retention interface sticking out the distal end of the conduit. It should be understood that other description of the retention device and central passageway presented elsewhere herein are applicable as well.

In some cases, the conduit may be configured to allow fluid flow between the paranasal sinus in the subject and the nasal cavity when the device is positioned within the stenotic opening. In some instances, the conduit is configured to allow fluid and/or air to flow from the paranasal sinus to the nasal cavity of the subject. For example, the conduit may be configured to facilitate drainage of fluid from the paranasal sinus in the subject to the nasal cavity when the device is positioned within the stenotic opening. In some cases, the conduit may be configured to facilitate the flow of air into and out of the paranasal sinus in the subject.

Aspects of the driver further include embodiments where the driver completely surrounds the conduit. The driver may be disposed on the exterior surface of the conduit around the entire periphery of the conduit. In certain embodiments, the driver surrounds the conduit around the central portion of the conduit, where the distal end of the conduit may have a distal anchor and the proximal end of the conduit may have a proximal anchor, as described in more detail herein. In some instances, the driver includes one or more subunits, where each subunit is disposed on the exterior surface of the conduit. The one or more driver subunits may be positioned such that they are in contact with the adjacent one or more driver subunits. Alternatively, the one or more driver subunits may be positioned such that there is a channel between the driver subunits. In certain instances, the channel between the driver subunits extends along the exterior surface of the conduit from the distal end of the conduit to the proximal end of the conduit. The channels may be configured to allow fluid and/or air to flow between the paranasal sinus and the nasal cavity of the subject.

In certain embodiments, the walls of the conduit are substantially rigid. The walls of the conduit may be substantially rigid, such that the conduit maintains substantially the same shape and size during use of the device. For instance, the conduit may maintain substantially the same interior diameter during use of the device. In some instances, the walls of the conduit are substantially rigid, such that pressure exerted on the exterior surface of the conduit by the driver does not significantly decrease the interior diameter of the conduit. For example, the walls of the conduit may be substantially rigid, such that the conduit is not crushed by the driver during use of the device. In some instances, the driver is configured to expand radially outward from the conduit. As discussed above, the conduit may be substantially rigid, thus expansion of the driver may be directed radially outward away from the substantially rigid walls of the conduit. Expansion of the driver radially outward from the conduit may facilitate dilation of the stenotic opening.

Aspects of the sinus dilator may include a distal anchor configured to maintain the device within the stenotic opening during use of the device. The distal anchor may be connected to the device proximal to the distal end of the device. For example, the distal anchor may be connected to the device proximal to the distal end of the conduit. In some cases, the distal anchor is configured to prevent the device from premature explantation from the stenotic opening. The distal anchor may facilitate maintaining the device within the stenotic opening for a desired period of time until the device is removed from the stenotic opening by the user or the health care provider. In certain embodiments, the distal anchor is a mechanical anchor, such as, but not limited to, a hook, a barb, a clamp, a tether and the like. In certain cases, the distal anchor is configured to maintain the device within the stenotic opening by having a diameter that is greater than the diameter of the stenotic opening.

In some cases, the distal anchor is configured to allow the device to be inserted into the stenotic opening. The distal anchor may have an outside diameter that is substantially the same as the outside diameter of the device when the device is in a non-expanded configuration. In some instances, the distal anchor has an outside diameter that is greater than the diameter of the conduit. In certain embodiments, the distal anchor has a tapered shape, such that the distal end of the distal anchor has a diameter that is less than the diameter of the proximal end of the distal anchor. In certain embodiments, the distal anchor is configured such that the distal anchor has a diameter that is smaller during insertion of the device into the stenotic opening as compared to the diameter of the distal anchor after the anchor portion of the device has been inserted into the paranasal sinus.

In certain embodiments, the distal anchor is a flexible anchor. In some cases, the flexible anchor is configured to fold into a configuration that has a smaller diameter during insertion of the device into the stenotic opening as compared to the diameter of the flexible anchor after the anchor portion of the device has been inserted into the paranasal sinus. For instance, the distal anchor may include one or more subunits that are connected to and extend radially outward from the conduit. The subunits of the anchor may be flexible, such that during insertion of the device into the stenotic opening, the subunits fold into a configuration where the anchor has an outside diameter that is less than the diameter of the distal anchor when the subunits are fully extended. Once the distal end of the device has been inserted into the paranasal sinus, the subunits may be free to unfold back to their extended configuration, thus anchoring the device within the stenotic opening.

Figure 13:
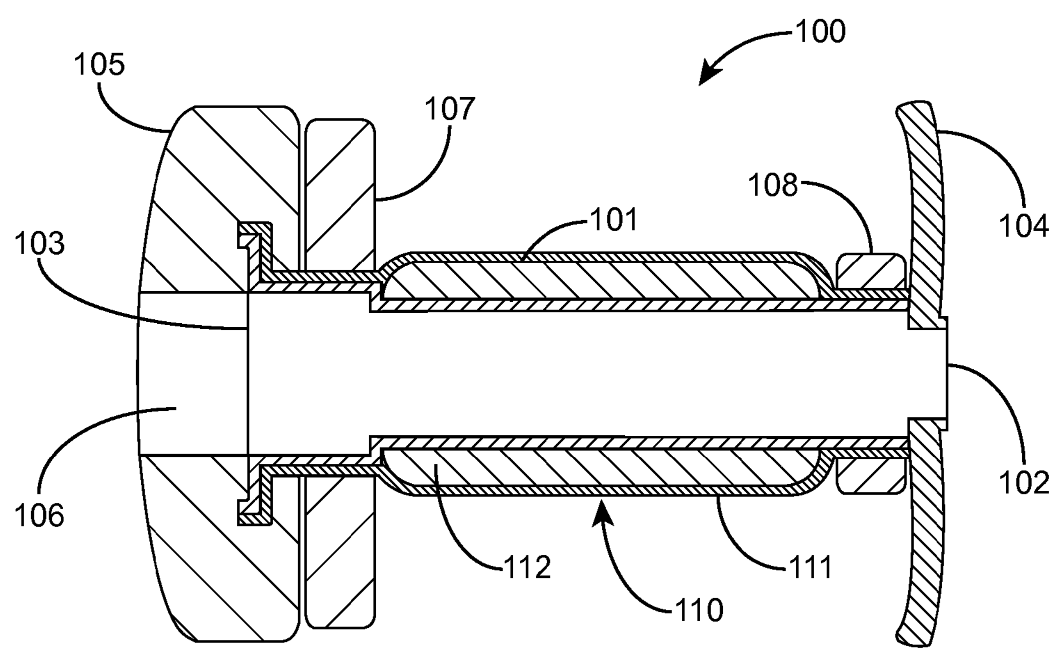
FIG. 13 is a sectional view of an osmotically driven device for dilating a paranasal sinus opening, in a non-expanded configuration, according to embodiments of the present disclosure.
Figure 14:
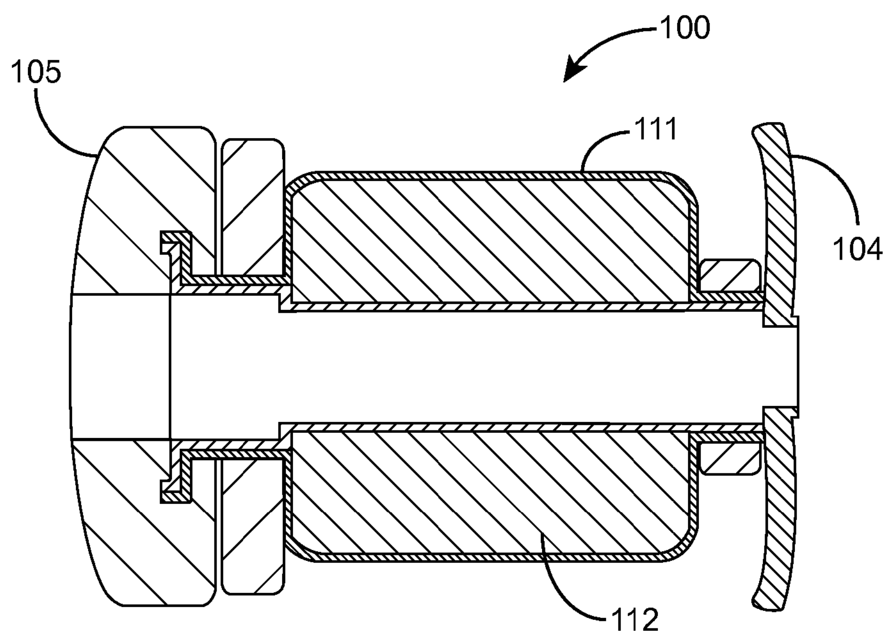
FIG. 14 is a sectional view of the device shown in FIG. 13, in an expanded configuration, according to embodiments of the present disclosure.

An embodiment of sinus dilator 100 is shown in FIGS. 13 and 14. FIG. 13 shows the sinus dilator 100 in a non-expanded configuration which is the configuration at the time the dilator is positioned within a sinus opening. FIG. 14 shows the sinus dilator 100 in an expanded configuration that is achieved after the dilator has been in place within a sinus opening. Sinus dilator 100 includes a tube 101 having a distal opening 102 and a proximal opening 103. Tube 101 has an inner diameter of 2 mm or more in order to permit bodily fluids such as mucus, puss and blood to drain out of the sinus and air to pass into and out of the sinus cavity while the sinus dilator 100 is positioned within the sinus opening. For those applications where sinus drainage is not a concern, or for shorter implantation durations, the tube 101 can be replaced by a solid member, e.g., a solid rod made of plastic or metal.

Figure 17:
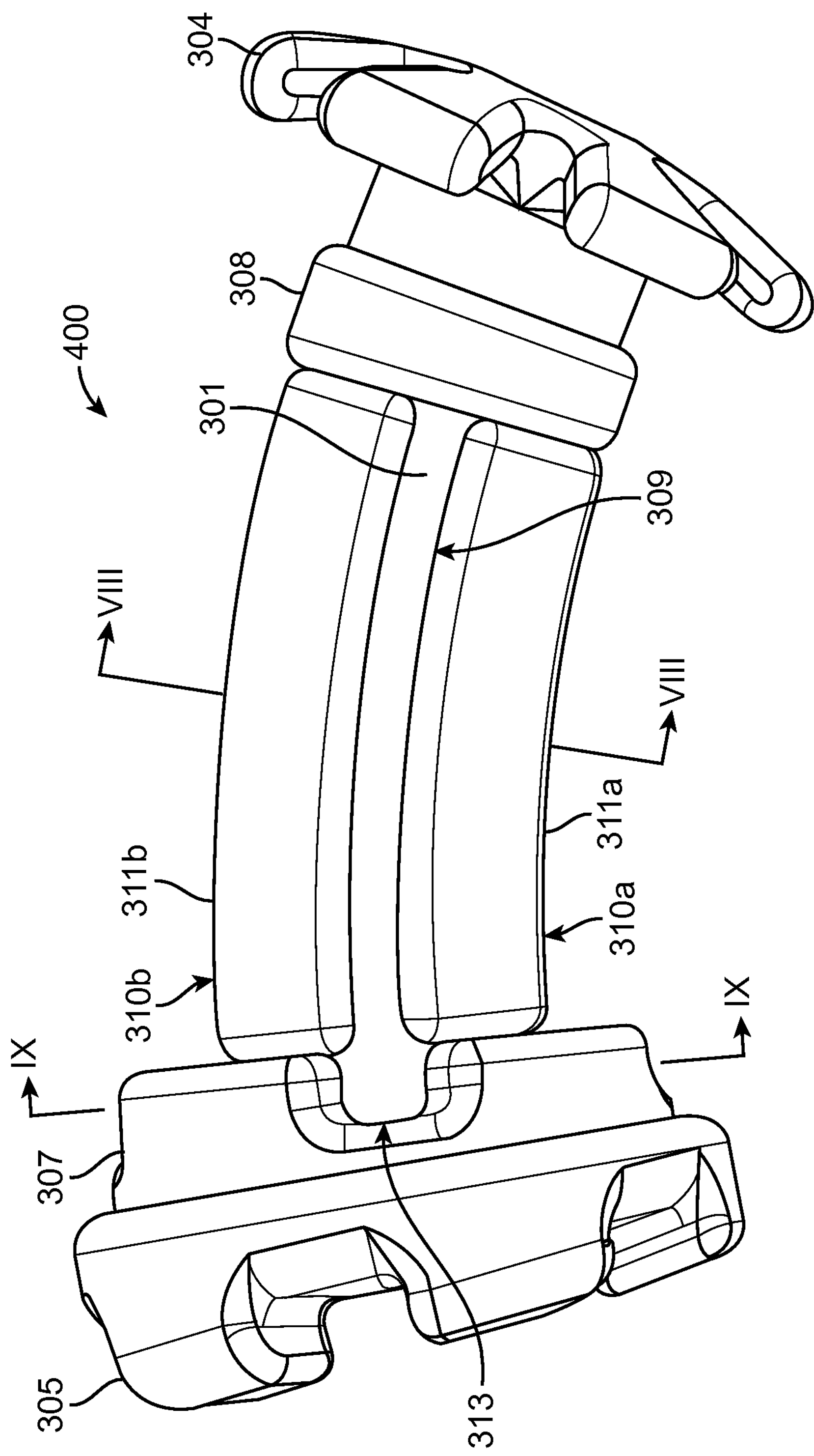
FIG. 17 is a side perspective view of an embodiment of an osmotically driven device for dilating a paranasal sinus opening, in a non-expanded configuration, according to embodiments of the present disclosure.

Positioned at the distal opening 102 is a flexible distal anchor 104. As used herein, the term "distal" refers to the end of the dilator that is first inserted into a paranasal sinus opening of the subject during use. Distal anchor 104 can have a daisy configuration as shown in FIG. 17 with flexible petals that can fold back onto the sinus dilator 100 as the distal end of the device is inserted through a sinus opening. Once in the opening, the petals spring back up and help keep the device from being prematurely expelled from the sinus opening into the nasal cavity.

Similarly, attached to the proximal end 103 of tube 101 is a proximal anchor 105 having a central passageway 106 which aligns with the hollow interior of tube 101. As used herein, the term "proximal" refers to the end of the dilator that remains on the nasal cavity side of the stenotic opening when the device is positioned in the stenotic opening during use. Proximal anchor 105 has an expanded diameter compared to the diameter of tube 101 and thereby acts as a second anchor for preventing the sinus dilator 100 from entering into the nasal sinus cavity during use. In certain embodiments, the opening 102, leading to the hollow interior of tube 101 and the aligned opening 106 create a conduit or passageway for fluid in the sinus cavity, such as mucus, puss and/or blood, to drain through the sinus dilator 100 while the sinus dilator 100 is positioned within the sinus opening.

Positioned along a central portion of tube 101 (e.g., between the distal anchor 104 and the proximal anchor 105) is an osmotic driver 110 that includes an elastic semipermeable membrane 111 surrounding an osmotic core 112. The osmotic core 112 may include one or more osmotically active agents such as water soluble salts or sugars, such as sodium chloride, lactose, etc., and optionally binders. The osmotic core additionally may include osmopolymers such as polyethylene oxide, sodium carboxymethyl cellulose, and the like. Once implanted into a paranasal sinus opening, water from the patient's body permeates through the membrane 111 by osmosis and forms a solution of the salt or sugar and hydrates the osmopolymer in the osmotic core 112, thereby causing the osmotic core 112 to expand. As water imbibes in, the volume of the core 112 increases, particularly due to the elastic nature of the membrane 111. The rate of water permeation can be controlled by controlling the composition, thickness and porosity of the membrane 111, in combination with the osmotic activity of the core 112. In the dilators disclosed herein, the membrane 111 composition, thickness and porosity are controlled to achieve expansion of the core 112 over a period of 0.25 days or more. In some cases, the expansion will occur gradually over a period of 0.25 to 14 days. In certain embodiments, the expansion will occur gradually over a period of 1 to 10 days. In other embodiments, the expansion will occur gradually over a period of 2 to 8 days. In this way the rapid expansion and the resulting pain experienced by the patient during conventional balloon sinuplasty is avoided.

Referring now to FIG. 14, there is shown an embodiment of sinus dilator 100 after it has been in place within a paranasal sinus opening. As can be seen by a comparison with the sinus dilator 100 shown in FIG. 13, the volume of the osmotic core 112 has expanded due to the imbibed water and the elastic semipermeable membrane 111 has stretched to accommodate this increased volume. In this way, the diameter of the core 112 has increased and when in place within the stenotic sinus opening exerts a radially outward force thereon, causing the sinus opening to dilate. The distal anchor 104 and the proximal anchor 105 facilitate maintaining the sinus dilator 100 positioned within the sinus opening during this radial expansion.

Also shown in FIGS. 13 and 14 are optional drug releasing reservoirs 107 and 108. Reservoir 107 is positioned near the proximal end of the device and may be configured to release drug at the nasal cavity end of the sinus opening. Reservoir 108 is positioned near the distal end of the dilator and may be adapted to release drug into the sinus itself. The reservoirs can be made from drug releasing materials including drug eluting polymers, bioerodible polymers such as PLGA, osmotically driven drug delivery systems, and sponges and similar matrices that are preloaded with drug, or in which a drug is added by the physician immediately before use of sinus dilator 100. The drugs that are placed in reservoirs 107 and 108 may be selected from antibiotics, anti-inflammatory drugs, anesthetics (e.g., local anesthetics), analgesics (e.g., locally acting analgesics), drugs that control, limit, or reduce bleeding (e.g., vasoconstrictors), combinations thereof, and the like. In certain embodiments, antibiotics include levofloxacin, moxifloxacin, amoxicillin, clavulanic acid, clarithromycin, azithromycin, cefuroxime, ciprofloxacin, salts thereof and combinations thereof and the like. In some instances, anti-inflammatory drugs include methylprednisolone, dexamethasone, salts thereof and combinations thereof and the like. In some cases, local anesthetics include lidocaine, bupivacaine, ropivacaine, tetracaine, salts thereof and combinations thereof and the like. In certain embodiments, locally acting analgesics include acetaminophen, Cox-2 inhibitors, such as celecoxib and rofecoxib and the like; NSAIDS such as diclofenac, ibuprofen, ketoprofen, naproxen, piroxicam, and aspirin and the like; and opioids such as morphine and tramadol and the like. In certain embodiments, vasoconstrictors include oxymetazoline, epinephrine, tranexamic acid, salts thereof, combinations thereof, and the like. In certain instances, the drug reservoirs may include a combination of drugs, such as a combination of an NSAID, an anti-inflammatory drug and a vasoconstrictor. For example, the drug may include OMS103HP (Omeros Corp., Seattle, Wash.), which includes an NSAID (ketoprofen), an anti-inflammatory drug (amitriptyline) and a vasoconstrictor (oxymetazoline). Alternatively or in addition to the drug reservoirs 107 and 108, the sinus dilator 100 may include a drug on the exterior surface of the dilator. For example, the sinus dilator 100 can be sprayed or coated with a drug solution or gel formulation prior to placement of sinus dilator 100 within the patient.

In certain embodiments, reservoirs 107 and 108 are composed of substantially rigid materials. In these embodiments, the reservoirs assist in directing the expansion of osmotic driver 110 in a radially outward direction, rather than in a direction that is parallel to the longitudinal axis of sinus dilator 100.

Figure 15:
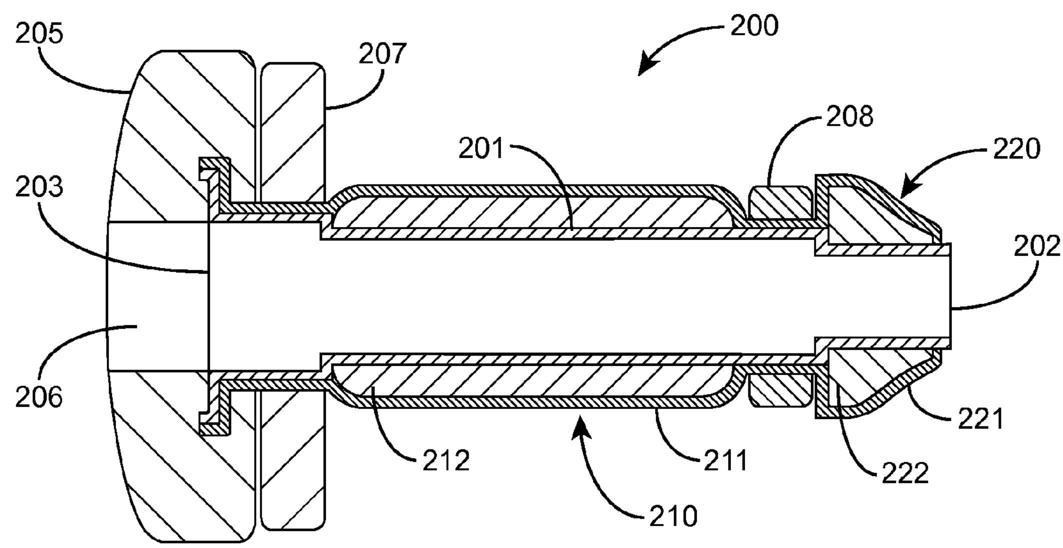
FIG. 15 is a sectional view of an embodiment of an osmotically driven device for dilating a paranasal sinus opening, in a non-expanded configuration, according to embodiments of the present disclosure.
Figure 16:
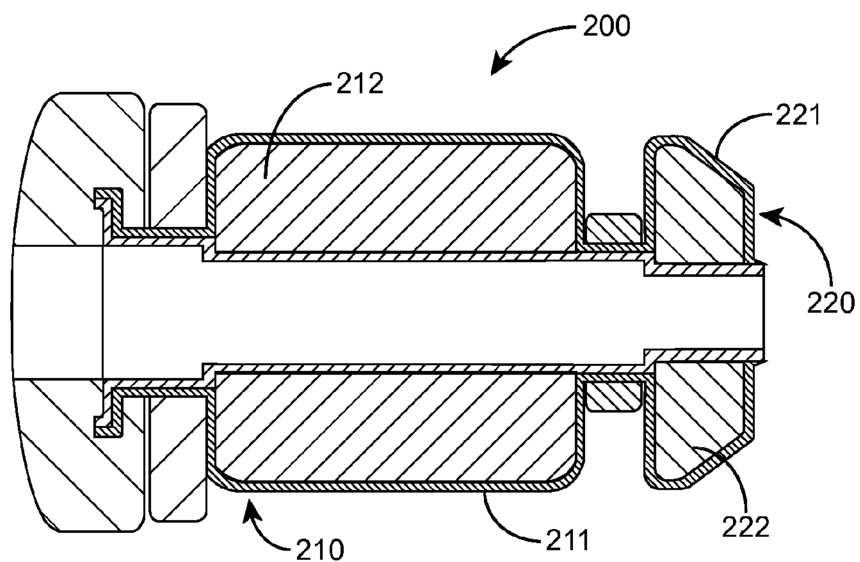
FIG. 16 is a sectional view of the device shown in FIG. 15, in an expanded configuration, according to embodiments of the present disclosure.

Reference is now made to FIGS. 15 and 16 which show an embodiment of an implantable dilation device 200. Similar to sinus dilator 100, device 200 also has a tube 201 with a distal opening 202 and a proximal opening 203; a proximal anchor 205 with a central passageway 206; an osmotic driver 210 including a semipermeable membrane 211 surrounding an osmotic core 212; and optional drug releasing reservoirs 207 and 208. Similar to sinus dilator 100, device 200 has an osmotic core 212 that gradually increases in volume over a period of 0.25 days or more to apply dilating force on the stenotic sinus opening, as shown in FIG. 16.

In place of the distal anchor 104 in sinus dilator 100, sinus dilator 200 has an osmotic anchor 220 including an elastic semipermeable membrane 221 surrounding an osmotic core 222. The operation of the osmotic driver 220 is similar to the operation of osmotic driver 110 in that osmotic core 222 may be configured to expand upon absorption of water from the patient's body. In certain embodiments, osmotic core 222 expands in volume at a rate greater than the rate of expansion of osmotic core 212. For example, osmotic core 222 may become fully expanded within several hours of insertion into the paranasal sinus opening, such as within 1 hour of insertion into the paranasal sinus opening. Driver 220 is shown in a fully expanded configuration in FIG. 16.

Referring now to FIG. 17, there is shown an embodiment of an implantable sinus dilator 400 that has a curved axis, which assists in the placement into certain sinus openings such as the maxillary sinus opening. Sinus dilator 400 has multiple osmotic drivers 310*a* and 310*b* separated by a channel 309. Each osmotic driver 310*a* and 310*b* includes an elastic semipermeable membrane 311*a* and 311*b*, respectively, and an osmotic core 312 (the osmotic core is shown in FIG. 8 but not in FIG. 7). Similar to the function and operation of sinus dilator 100, sinus dilator 400 also has a proximal anchor 305 at its proximal end, a distal anchor 304 at its distal end; and optional drug releasing reservoirs 307 and 308.

Figure 21:
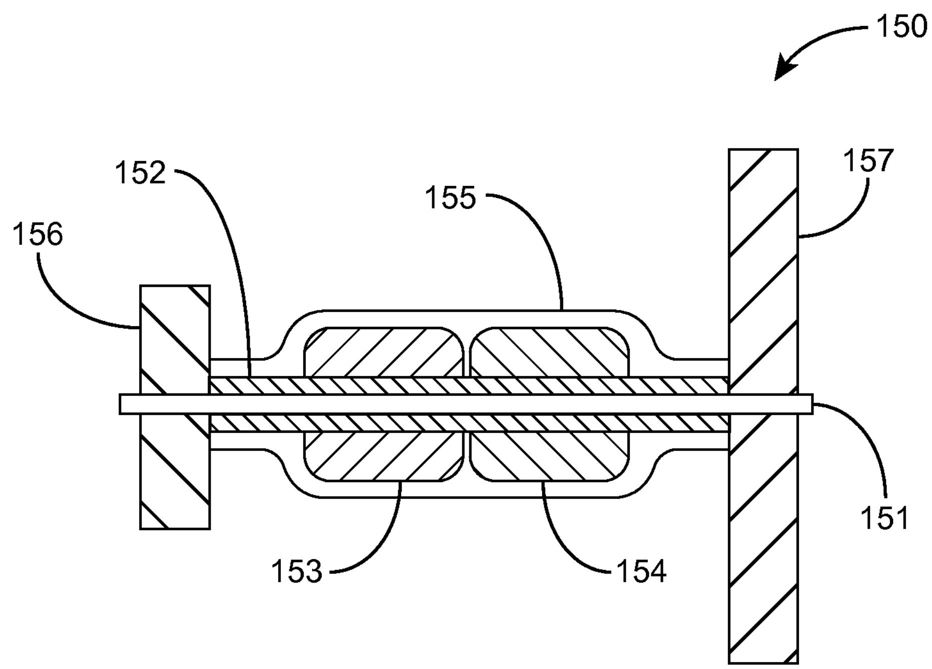
FIG. 21 is a sectional view of an osmotically driven device for dilating a paranasal sinus opening, in a non-expanded configuration, according to embodiments of the present disclosure.
Figure 22:
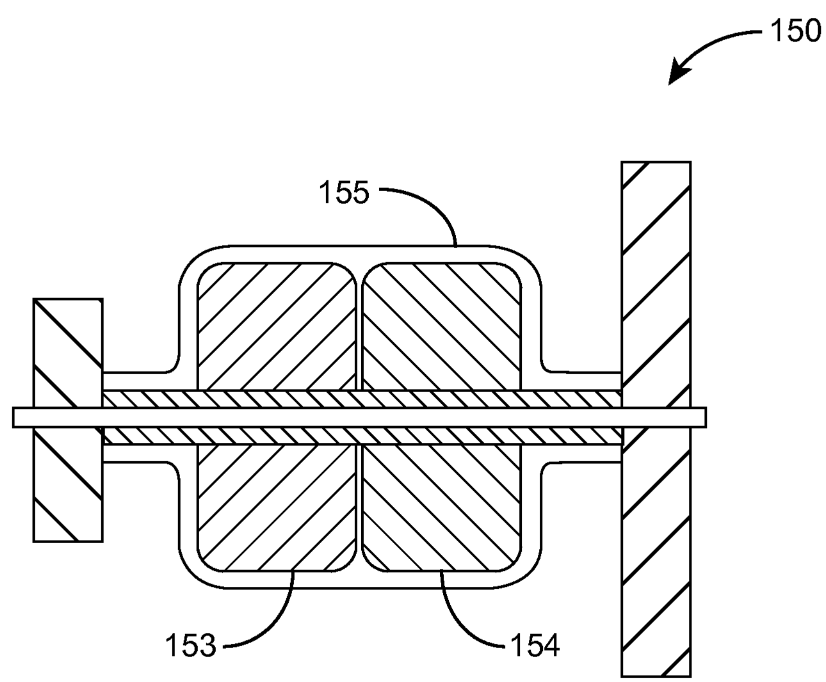
FIG. 22 is a sectional view of the device shown in FIG. 21, in an expanded configuration, according to embodiments of the present disclosure.

Another embodiment of an osmotic dilator 150 is shown in a non-expanded configuration in FIG. 21 and in an expanded configuration in FIG. 22. Dilator 150 includes tube 151 (e.g., a stainless steel tube) having an inner membrane coating 152 disposed thereon. Two osmotic salt tablets 153, 154 are threaded onto the coated tube 151. An external elastic semipermeable membrane coating 155 is applied thereover. The dilator 150 includes distal and proximal anchors 156, 157 respectively, which may be attached (e.g., glued) to the tube 151 to secure the anchors to the tube 151.

As shown in FIGS. 21 and 22, certain embodiments of the osmotic core include ring (e.g., donut) shaped salt- and polymer-containing tablets 153, 154 having an inner opening that is large enough to slide over tube 151. In some instances, the tablets have an outer diameter of 5 mm or less, such as 4 mm or less, or 3 mm or less, or 2 mm or less, or 1 mm or less. For instances, the tablets may have an outer diameter of 3 mm. In some instances, the salt tablets 153, 154 are composed of a salt (e.g., NaCl). In certain cases, the tablets are composed of a polymer, such as a high molecular weight hydrogel-forming polymer, for example polyethylene oxide (e.g., Polyox™, The Dow Chemical Company, Midland, Mich.). In certain cases, the tablets include tableting excipients and/or lubricants. In some embodiments, the tablets include 10 to 95 wt % salt, such as 20 to 90 wt % salt, including 30 to 80 wt % salt, or 40 to 70 wt % salt. For example, the tablets may include 10 to 95 wt % NaCl, such as 20 to 90 wt % NaCl, including 30 to 80 wt % NaCl, or 40 to 70 wt % NaCl. In some cases, the tablets include 30 to 80 wt % NaCl. In certain embodiments, the tablets include 5 to 90 wt % polymer, such as 10 to 80 wt % polymer, including 20 to 70 wt % polymer, or 30 to 60 wt % polymer. For example, the tablets may include 5 to 90 wt % Polyox, such as 10 to 80 wt % Polyox, including 20 to 70 wt % Polyox, or 30 to 60 wt % Polyox. In certain cases, the tablets include 20 to 70 wt % Polyox. In some embodiments, the tablets are composed of a salt and a polymer, as described above. For example, the tablets may include 30 to 80 wt % NaCl and 20 to 70 wt % Polyox. In certain instances, the NaCl gives a quicker rate of expansion than does the Polyox, though both materials are osmotically active and cause water to be imbibed into the interior of the dilator 150. Because of its low molecular weight, there may be some leakage of NaCl out through the semipermeable membrane 155, whereas because of its high molecular weight, there is substantially no leakage of the Polyox out through the semipermeable membrane 155. A higher NaCl loading (e.g., 80 wt %) gives a longer duration of dilator 150 expansion than a lower NaCl loading (e.g., 20 wt %).

The osmotic dilator 150 has been fabricated as follows. Passivated, stainless steel tubes 151 were dipped into a semipermeable membrane coating solution multiple times to build up an inner membrane coating 152 on the tube having a thickness of 0.005 inch (0.013 cm). The tubes 151 were hung vertically and dried in a current of room temperature air in a fume hood between coatings. Two osmotic salt tablets 153, 154 comprised of NaCl and polyethylene oxide hydrogel were threaded onto the coated stainless steel tube 151. The pair of osmotic tablets 153, 154 were positioned in the middle of the tubes 151 and set such that they were in contact with each other. The resulting subassembly was then dip coated in the same semipermeable membrane coating solution multiple times until an external elastic semipermeable membrane coating 155 having a thickness of 0.015 inch (0.038 cm) was built up. The subassemblies were hung vertically and dried between coatings. To promote evenness of coating thickness, the tubes 151 were rotated 180° between coatings. The final coated subassembly was dried at room temperature in a current of air for 2 days. After drying, excess membrane material was removed from each end of the tubes 151 using a razor blade. The portion removed spanned the distance of 2 mm from the edge of the osmotic drivers 153, 154 to the ends of the tubes 151. The tubes 151 were cut off at each end, with the cuts being 4 mm from the edge of the osmotic salt tablets 153, 154, leaving an overall dilator 150 length of 13 mm.

Distal and proximal anchors 156, 157 were fabricated. The proximal anchor 157 was punched from 1.7 mm sheet stock of black acrylonitrile butadiene rubber (Buna-n) in the outline shape of a dog bone. The length of the proximal anchor was 10.3 mm and the width, at the necked-down portion, was 6.5 mm. A hole was drilled through the center of the anchor using a 0.042 inch (0.11 cm) drill bit. The distal anchor 156 was made of molded black polyurethane (grade 60A) rubber having a central hole similar in size to the drilled hole of the proximal anchor 157. The distal anchor 156 had a daisy petal configuration with an outside diameter of 6.2 mm. The distal and proximal anchors 156, 157 were affixed to the stainless steel tube 151 by threading the ends of the tube 151 into the holes in the anchors 156, 157 and secured using a medical grade cyanoacrylate adhesive (Loctite 4013, Loctite Corp., Rocky Hill, Conn.).

Figure 23:
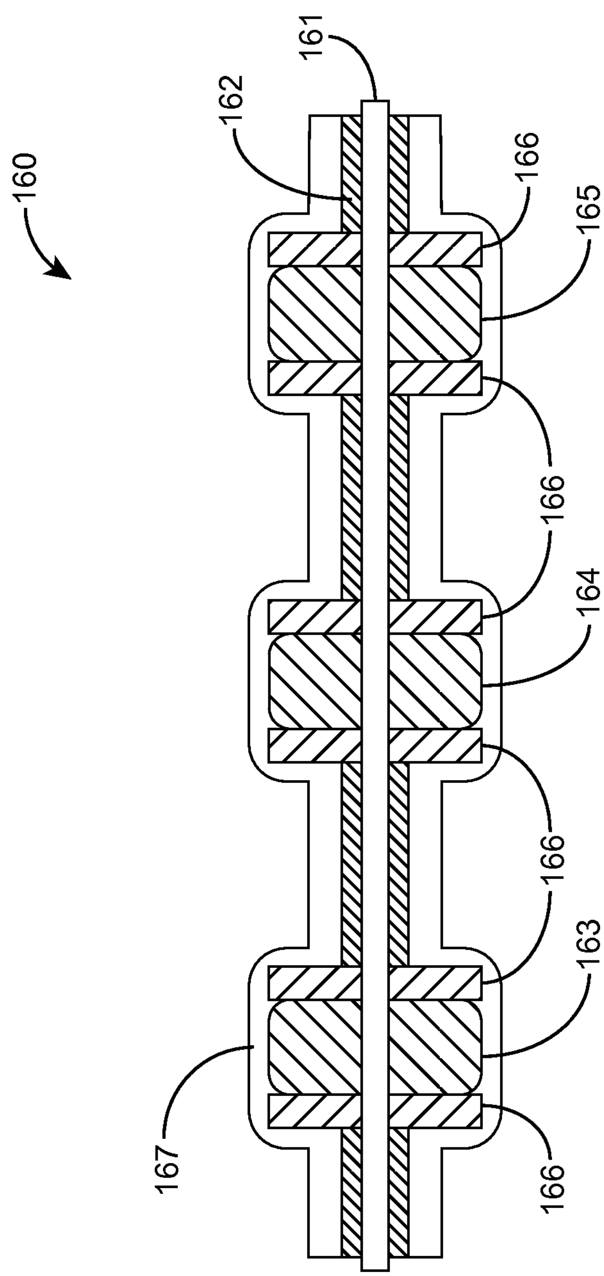
FIG. 23 is a sectional view of an osmotically driven device for dilating a paranasal sinus opening, in a non-expanded configuration, according to embodiments of the present disclosure.

A self-positioning (e.g., self-centering) sinus ostium dilator 160 having spaced salt tablets 163, 164, 165 is shown in FIG. 23. Dilator 160 has been made as follows. Pieces of 304 stainless steel tube stock 161 having an inside diameter of 0.032 inch (0.081 cm), an outside diameter of 0.042 inch (0.11 cm) and a length of 55 mm were dip coated in an elastomeric semipermeable membrane coating solution comprising a 10 wt % solids solution of polyurethane (Tecophilic grade HP60D-20; Thermedics™ Polymer Products, Wilmington, Mass.) dissolved in n-methyl pyrrolidone. The tubes 161 were dip coated multiple times until a membrane coating 162 having a nominal coating thickness of 0.005 inch (0.01 cm) had accumulated on the middle of each of the tubes 161. The tubes 161 were dried in a current of room temperature air between coatings. Polyether ether ketone polymer stock was machined to form microwashers 166 having an inner opening diameter of 0.055 inch (0.14 cm), an outside diameter of 0.110 inch (0.28 cm) and a thickness of 0.020 inch (0.05 cm). The average weight of the microwashers 166 was 3 mg. Three osmotic salt-containing tablets 163, 164, 165 equivalent to those used in dilator 150 and six microwashers 166 were then threaded onto the coated stainless steel tubes 161 such that a microwasher 166 was placed in contact with each tablet as shown in FIG. 23, forming three distinct sets of microwasher+salt tablet+microwasher sandwiched subassemblies. Additionally, a 1.5 mm gap was provided between the middle and the end subassemblies. Next, the tubes 161 with subassemblies were dip coated multiple times in the same membrane coating solution until a continuous elastomeric semipermeable membrane coating 167 on the salt tablets 163, 164, 165 was developed. Between dip coatings, the dilators 160 were dried in a current of room temperature air. At each coating, the middle salt tablet 164 and one of the two end salt tablets 163, 165 were coated. Then, on the next application, the dilator was inverted 180° and the middle salt tablet 164 was coated again and the other of the two end salt tablets 163, 165 was coated. In such a process, the middle salt tablet 164 accumulated a thicker membrane 167 coating, due to more coats, than the end salt tablets 163, 165 such that at the completion of the coating cycle, the middle salt tablet 164 had a coating thickness of 0.021 inch (0.053 cm) while the end salt tablets 163, 165 had coatings with thickness values in the range of 0.015 to 0.017 inch (0.038 to 0.043 cm). Proximal and distal anchors as described in connection with dilator 150 (not shown in FIG. 23) are optionally attached the ends of the tubes 161.

When in an aqueous environment such as a sinus ostium (e.g., a maxillary sinus ostium), the osmotic dilators 160 imbibe physiological fluids causing radial distension of the outer elastomeric semipermeable membrane 167. The end salt tablets 163, 165 imbibe fluid at a faster rate than the middle salt tablet 164 which has a thicker coating of membrane 167. The net result of these different imbibition rates is that the dilator 160 forms a dumb bell configuration that helps to nest and position the dilator within the sinus ostium. The microwashers serve to direct swelling radially outwardly to further improve ostium dilation.

Figure 18:
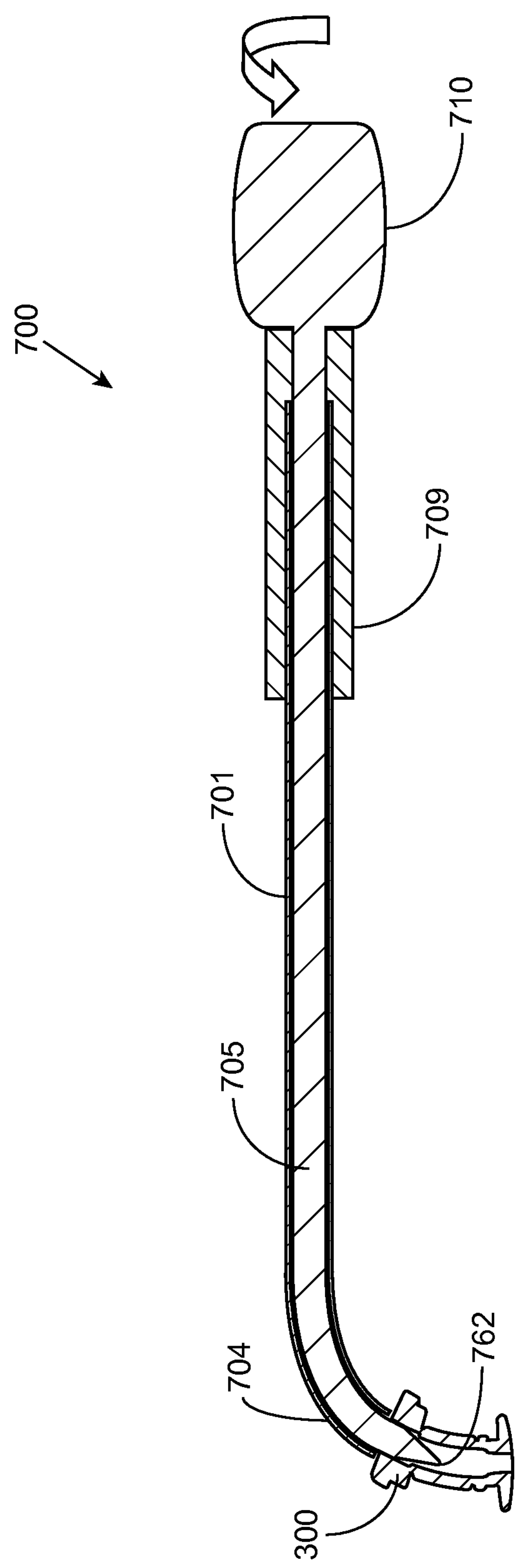
FIG. 18 is a side sectional view of an implantation device 700 with a sinus dilator 300 coupled therewith, according to some embodiments.
Figure 19:
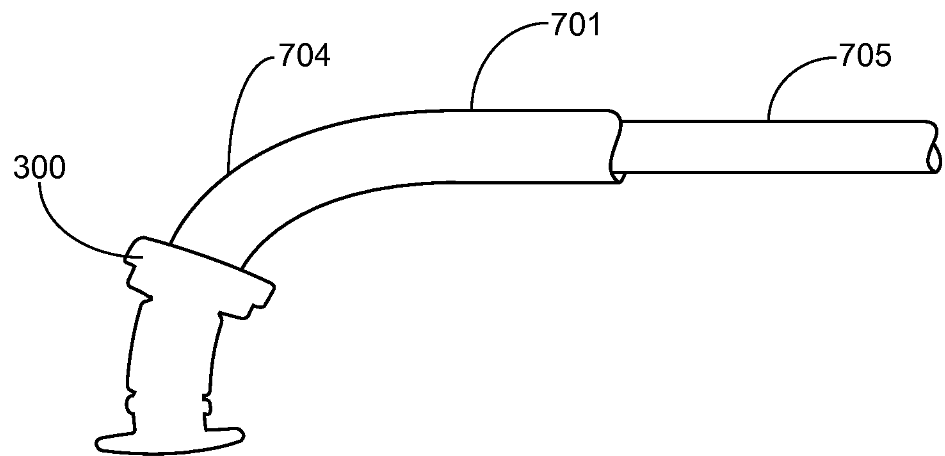
FIG. 19 is a side partial cutaway view of the distal end of the implantation device 700 shown in FIG. 18.
Figure 20:
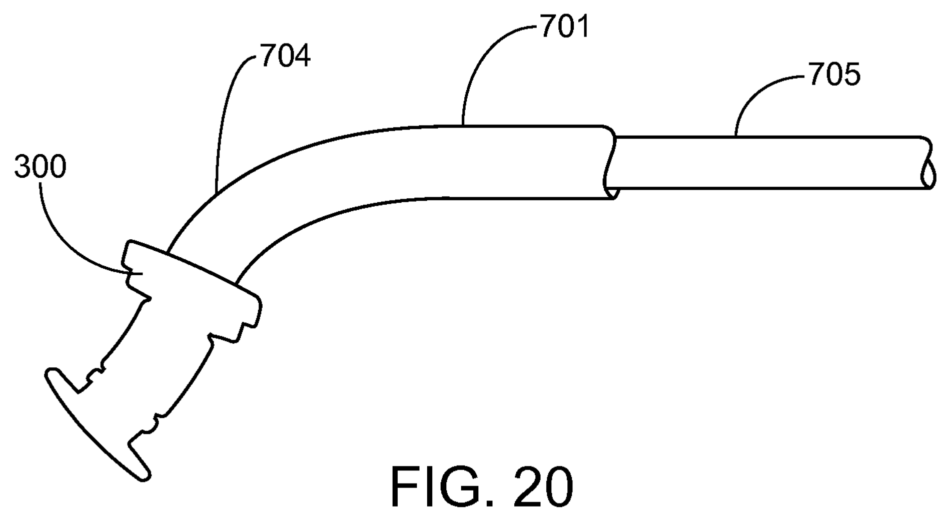
FIG. 20 is a side partial cutaway view of the distal end of the implantation device 700 shown in FIG. 18.

The implanter can optionally include a steering feature to facilitate placement of the sinus dilator. Such a steerable implanter can be particularly useful in those situations where the pathway to the sinus opening is either partially blocked or otherwise involves a non-linear pathway from the nostril opening. FIG. 18 illustrates a side sectional view of an example of a steerable implantation device 700 with a sinus dilator 300 coupled therewith. Implantation device 700 comprises a handle 710 coupled to the proximal end of a hollow elongated member 701. At the distal end of the hollow elongated member 701 (e.g., cannula), sinus dilator 300 is coupled to a retention interface 762 on interior elongated member 705 extending within the hollow elongated member 701. The hollow elongated member has a curved tip section 704. The dimensions and tip curvature of the hollow elongated member 701 may vary to facilitate implantation of the sinus dilator 300 into specific paranasal sinuses, such as a frontal sinus, a sphenoid sinus or a maxillary sinus. Coupled to elongated member 705 is a knob 710. Axial rotation of knob 710 in the direction of the arrow while holding handle 709 relatively stationary causes the member 705 to rotate within hollow elongated member 701. In the case of a sinus dilator 300 having a curved axis, this axial rotation of knob 710 can be used to assist the operator to position dilator 300 within a sinus opening. Rotation of knob 710 relative to the handle 709 causes the dilator 300 to be angled in different orientations as is best shown in FIGS. 19 and 20. Thus, FIG. 19 shows the distal end of device 700 with the knob 710 in an initial rotational position, while FIG. 20 shows the distal end of device 700 with the knob 710 rotated approximately 180 degrees from the initial position.

In an alternative embodiment, the hollow elongated member 701 does not have a curved tip section 704 and the interior elongated member 705 may be rotated by a knob 710 coupled to the interior elongated member 705. For example, in some instances, a sinus dilator 300 having a curved axis may be coupled to the implantation device and reoriented by rotating knob 710.

Methods

In some aspects of the present disclosure, methods of implanting a sinus dilator in the stenotic opening of a paranasal sinus in a subject are provided. In certain embodiments, the methods may include coupling a sinus dilator to a retention interface of an interior elongated member positioned within a hollow elongated member of an implantation device. For example, the sinus dilator may slide onto the retention interface that is shaped to be inserted into the central passageway of the sinus dilator. Stops and retention elements may be included to maintain the sinus dilator in place when coupled to the retention interface. In some instances, the sinus dilator may abut the hollow elongated member when completely inserted on the retention interface.

The sinus dilator and distal end of the hollow elongated member of the device are then inserted into the nasal cavity of the subject. The sinus dilator is positioned into the stenotic opening. This may require a variable amount of force depending on how occluded the stenotic opening is. For example, the sinus dilator may be inserted within the stenotic opening such that an anchor at the distal end of the sinus dilator is inserted through the stenotic opening and positioned within the sinus cavity. The anchor secures the sinus dilator such as to hold onto the sinus dilator when the retention interface is withdrawn. The anchor may also assist in overcoming any additional securing force provided by retaining elements if present. A trigger may then be actuated causing a relative displacement of the interior elongated member with respect to the hollow elongated member such that at least a portion of the retention interface that is outside of the distal end of the interior elongated member is relatively displaced within the hollow elongated member. The sinus dilator is decoupled from the retention interface during the relative displacement and maintained in the stenotic opening. The hollow elongated member of the device is then removed from the nasal cavity of the subject.

In some embodiments, the relative displacing of the interior elongated member with respect to the hollow elongated member includes proximally displacing the retention interface within the hollow elongated member while the hollow elongated member remains in a relatively fixed position to the handheld member. For example, the implantation device may include coupling mechanism, such as a protrusion on a trigger arm that mates with a notch on the interior elongated member. As the trigger is displaced proximally in a slot on the handheld member, the interior elongated member is displaced proximally causing the retention interface to displace such that at least a portion of the retention interface that is outside of the distal end of the interior elongated member is displaced within the hollow elongated member. In some instances, the distal tip of the hollow elongated member pushes the sinus dilator as all or part of the retention interface is displaced within the hollow elongated member.

In other embodiments, the relative displacing of the interior elongated member with respect to the hollow elongated member includes distally displacing the hollow elongated member away from the handheld member while the retention interface and interior elongated member remain in a relatively fixed position to the handheld member. For example, the implantation device may include coupling mechanism, such as a notch on a trigger arm that mates with a protrusion on the hollow elongated member. As the trigger is slidably displaced in a slot on the handheld member, the hollow elongated member is displaced distally away from the handheld member causing the distal tip of the hollow elongated member to push the sinus dilator as all or part of the retention interface is displaced within the hollow elongated member.

In certain embodiments, the method includes contacting the sinus dilator with a fluid prior to positioning the device in the stenotic opening. For embodiments of the device that include a swellable polymer or an osmotic agent, contacting the sinus dilator with a fluid prior to insertion into the stenotic opening may facilitate expansion of the sinus dilator after positioning the sinus dilator in the stenotic opening. For example, embodiments of the device may be configured to begin expanding 30 min or more, such as 45 min or more, including 60 min or more, or 90 min or more, 120 min or more, or 180 min or more after the device has been contacted with a fluid. In these embodiments, contacting the sinus dilator with a fluid prior to insertion of the sinus dilator into the stenotic opening may facilitate the onset of expansion of the sinus dilator at a point in time sooner after insertion of the sinus dilator into the stenotic opening. In some instances, the fluid may include water, saline, sterile water, sterile saline, and the like.

In some embodiments, methods further comprise dispensing fluid to the sinus cavity or nasal cavity via a lumen or fluid carrying tube within the interior elongated member or hollow elongated member. For example, in some instance, a lumen may be provided within the interior elongated member and may connect to a fluid carrying tube in the handheld member. Example fluids that may be dispensed are, for example, fluids comprising water, saline solution, drugs, etc. Example drugs that may be present in the fluid (e.g., in fluid or solid form) may include, but are not limited to fluids comprising one or more analgesics, anesthetics, anti-inflammatories, antibiotics, steroids, drugs that control or limit bleeding (e.g., vasoconstrictors), etc. Vasoconstrictors may include, for example, oxymetazoline, epinephrine, tranexamic acid, salts thereof, combinations thereof, and the like. In some instances, the methods may further comprise dispending solid pellets, or other forms of solids (e.g., powder), from the lumen being coupled to a tube connected to a pellet source (or other corresponding source of solid substance). In other instances, the lumen may be coupled to a tube connected to a suction source (e.g., vacuum source) to provide suction to remove fluids and/or small tissue out of the sinus cavity or nasal cavity.

In some embodiments, methods further comprise visualizing the stenotic site via a camera positioned near the distal end of the hollow elongated member. In some instances, the camera may be positioned on the exterior surface of the hollow elongated member and electrically coupled to a monitor via an electrical wire extending along or within the hollow elongated member. In other instances, the camera may be positioned within the hollow elongated member. For example, a camera may be inserted at the tip of the interior elongated member and electrically coupled to a monitor via an electrical wire extending within the interior elongated member.

Some methods may include removing the sinus dilator from the stenotic opening at a point in time after the sinus dilator has expanded to the expanded configuration. The sinus dilator may be removed by contacting a removal device to the sinus dilator and extracting the sinus dilator from the stenotic opening. In some cases, the removal device may be attached to the sinus dilator using a hook, a loop, a clamp, a suction device, and the like. For instance, the removal device may include a hook configured to attach to a loop on the sinus dilator. Removal of the sinus dilator may be achieved by pulling the sinus dilator from the stenotic opening. In certain embodiments, removal of the sinus dilator may be facilitated by reducing the internal pressure of the driver before removing the device from the stenotic opening. In some cases, the internal pressure of the driver may be reduced by puncturing the driver. For example, the removal device may include a needle or blade configured to create a hole in the driver allowing the internal pressure of the driver to equalize with the pressure in the nasal cavity. In some cases, the removal device may include a suction device configured to remove the internal contents of the driver from the sinus dilator, thus reducing the pressure the device is exerting on the surrounding stenotic opening.

Systems

Aspects of the present disclosure include a system for inserting a sinus dilator for dilation of a stenotic opening of a paranasal sinus in a subject. The systems include a device for dilating the stenotic opening and an implantation device configured to position the device in the stenotic opening. The implantation device may include a handheld member, a hollow elongated member coupled to the handheld member, an interior elongated member within the hollow elongated member and including a retention interface to removably couple to the sinus dilator, as described herein.

Utility

The subject devices, systems, and methods find use in a variety of different applications where an implanted sinus dilator is necessary to dilate a stenotic opening of a paranasal sinus in a subject. In certain embodiments, the methods are directed to implantation of sinus dilators for a patient having sinusitis.

As described above, the method may include coupling a sinus dilator to the retention interface of the interior elongated member of the implantation device described in the present disclosure; inserting the sinus dilator and distal end of the hollow elongated member of the device into the nasal cavity of the subject; positioning the sinus dilator into the stenotic opening; decoupling the sinus dilator from the implantation device; and removing the hollow elongated member of the device from the nasal cavity of the subject.

Implantation of a sinus dilator within the stenotic opening of paranasal sinus enables dilation of the stenotic opening of the paranasal sinus to facilitate an alleviation of the symptoms associated with sinusitis. For instance, dilation of the stenotic opening may allow a greater amount of drainage through the stenotic opening as compared to the undilated stenotic opening. Dilation of the stenotic opening may also facilitate the flow of air into and out of the paranasal sinus, which may help alleviate the symptoms associated with sinusitis.

The subject devices, systems, and methods may also facilitate the treatment of a patient having a sinus dilator implanted by delivering a drug (e.g., an anesthetic; an analgesic; an antibiotic; a steroid; an anti-inflammatory; a drug to control, reduce or limit bleeding, etc.) to nasal or sinus cavity during, after, or before implantation to alleviate pain, reduce swelling, sanitize within the cavity, reduce bleeding, etc. As described herein, the device may be coupled to (i) fluid sources (e.g., drug sources, saline sources, etc.) that enable the device to dispense the fluid from the distal end of the device into the nasal and/or sinus cavity; and/or (ii) vacuum sources to provide suctioning.

Kits

Also provided are kits for use in practicing the subject methods, where the kits may include one or more of the above implantation devices, and/or sinus dilators, as described above. As such, a kit may include an implantation device, and may further include one or more sinus dilators. In some instances, a sinus dilator may come preloaded on the implantation device. In some instances, the sinus dilators may come decoupled from the implantation device.

In some instances, the kit may further include additional components, such as fluid sources (e.g., water sources, saline solution sources, drug solution sources, etc.), connective tubing, monitor, etc., which may find use in practicing the subject methods. The drugs may be provided in a separate container, such as a syringe, vial, bottle, etc., such that the drug may be filled into the drug reservoir of the device prior to insertion of the device into the stenotic opening. The drugs sources may be adapted to couple with the implantation device, such as a cartridge that is coupled to a receiving slot in the implantation device, or such as a container that is coupled to a port on the implantation device via tubing.

Furthermore, where the retention interface of the implantation device is removably coupled to the interior elongated member, the kit may further include one or more additional or different retention interfaces. Such may be desirable where the kit includes sinus dilators of different sizes and/or types, or for convenience for sanitation purposes. Various components may be packaged as desired, e.g., together or separately.

In certain embodiments, the kits include one or more sinus ostium sizing probes. In some instances, the probes are configured to be removably mountable onto the distal end of the dilator insertion/implanting devices (e.g., on the distal end of the hollow elongated member of the device). In certain cases, the probes are of varying diameters and adapted to be inserted into the dilated ostium to determine the diameter of the dilated ostium and assess whether further dilation is needed. When using the device 900 of FIG. 24, such probes can be made from light-transmitting materials in order to illuminate the probes during dilated ostium measurement.

In addition to above mentioned components, the subject kits may further include instructions for using the components of the kit to practice the subject methods. The instructions for practicing the subject methods may be recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g. CD-ROM, diskette, DVD, Blu-Ray, computer-readable memory, etc. In yet other embodiments, the actual instructions are not present in the kit, but means for obtaining the instructions from a remote source, e.g. via the Internet, are provided. An example of this embodiment is a kit that includes a web address where the instructions can be viewed and/or from which the instructions can be downloaded. As with the instructions, this means for obtaining the instructions is recorded on a suitable substrate.

Although the foregoing embodiments have been described in some detail by way of illustration and example for purposes of clarity of understanding, it is readily apparent to those of ordinary skill in the art in light of the teachings of the present disclosure that certain changes and modifications may be made thereto without departing from the spirit or scope of the appended claims. It is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein.

What is claimed is:

1. A kit comprising:

a self-expanding sinus dilator comprising a self-expanding driver comprising one or more of an osmotic agent and a swellable agent, wherein the self-expanding driver expands from a non-expanded configuration to an expanded configuration upon absorbing fluid from the surrounding environment; and a device for inserting the self-expanding sinus dilator into a stenotic opening of a paranasal sinus of a patient, the device comprising:

a handheld member including a handle;

a hollow elongated member having a proximal end coupled to the handheld member and a distal end having an opening to an interior cavity of the hollow elongated member;

an interior elongated member extending within the interior cavity of the hollow elongated member, wherein the handheld member comprises a trigger capable of moving the interior elongated member relative to the hollow elongated member; and a retention interface for removably coupling to the self-expanding sinus dilator, the retention interface positioned proximate to the distal end of the hollow elongated member;

wherein activation of the trigger causes the retention interface to decouple from the self-expanding sinus dilator.

2. The kit of claim 1, wherein the retention interface is relatively displaceable with respect to the hollow elongated member.

3. The kit of claim 1, wherein upon actuation of the trigger, the hollow elongated member remains in a relatively fixed position to the handheld member and the retention interface is displaced proximally relative to the hollow elongated member.

4. The kit of claim 3, wherein the trigger is slidably coupled to the hand held member and coupled to the interior elongated member such that sliding the trigger displaces the retention interface proximally.

5. The kit of claim 1, wherein the retention interface has a smaller cross-sectional width than a portion of the interior elongated member within the hollow elongated member.

6. The kit of claim 5, wherein the retention interface and the interior elongated member are a single unitary piece of a material.

7. The kit of claim 1, wherein the retention interface has a cross sectional width that decreases towards a distal tip of the retention interface.

8. The kit of claim 1, comprising a light source for illuminating the dilator during insertion.

9. The kit of claim 1, wherein the distal end of the hollow elongated member is curved.

10. The kit of claim 1, wherein the retention interface comprises a split tip.

11. The kit of claim 1, comprising a lumen extending within the interior elongated member and having an opening at a distal tip of the interior elongated member.

12. The kit of claim 11, wherein the lumen is coupled to a fluid source comprising a fluid including at least one drug selected from the group consisting an analgesic, an anesthetic, an anti-inflammatory, an antibiotic, a steroid, and a drug that limits bleeding.

13. The kit of claim 11, wherein the lumen is coupled to a source of suction.

14. The kit of claim 1, wherein the self-expanding sinus dilator is removably coupled to the retention interface.

15. The kit of claim 1, comprising a fluid source adapted to couple to the device and provide fluid to be dispensed out of the device into a sinus or nasal cavity of the subject.

16. The kit of claim 1, comprising one or more retention interfaces configured to be removably coupled to the interior elongated member of the device.

17. The kit of claim 1, wherein the self-expanding sinus dilator is coupled to the device.

18. The kit of claim 1, comprising one or more sinus ostium sizing probes, the probes being adapted to be removably mounted on the distal end of the hollow elongated member of the device.

19. The kit of claim 1, wherein the osmotic agent comprises a salt, a sugar, an osmopolymer, or combinations thereof.

20. The kit of claim 19, wherein the osmotic agent comprises sodium chloride, lactose, polyethylene oxide, sodium carboxymethyl cellulose, or combinations thereof.

21. The kit of claim 1, wherein the one or more of the osmotic agent and the swellable agent comprises polyethylene oxide or sodium carboxymethyl cellulose.

22. The kit of claim 1, wherein the one or more of the osmotic agent and the swellable agent comprises sodium chloride and polyethylene oxide.

23. A method of using the kit of claim 1 to dilate a stenotic opening of a paranasal sinus in a subject, the method comprising:

coupling the self-expanding sinus dilator to the retention interface of the device;

inserting the self-expanding sinus dilator and distal end of the hollow elongated member of the device into a nasal cavity of the subject;

positioning the self-expanding sinus dilator into the stenotic opening;

decoupling the retention interface from the self-expanding sinus dilator; and removing the hollow elongated member of the device from the nasal cavity of the subject.

24. The method of claim 23, wherein decoupling the retention interface comprises relatively displacing the interior elongated member with respect to the hollow elongated member, wherein the self-expanding sinus dilator is decoupled from the retention interface during the relative displacement and maintained in the stenotic opening.

25. The method of claim 24, wherein the relative displacing of the interior elongated member with respect to the hollow elongated member comprises proximally displacing the retention interface relative to the hollow elongated member while the hollow elongated member remains in a relatively fixed position to the handheld member.

26. The method of claim 23, comprising dispensing fluid to the nasal or sinus cavity via a lumen positioned within the hollow elongated member, wherein the fluid comprises at least one drug selected from the group consisting of an analgesic, an anesthetic, an anti-inflammatory, an antibiotic, a steroid, and a drug that limits bleeding.

27. The method of claim 23, comprising suctioning fluid or debris from the nasal cavity or sinus cavity via a lumen positioned within the hollow elongated member.

28. The method of claim 23, comprising visualizing the stenotic opening via a camera positioned near the distal end of the hollow elongated member.

29. The method of claim 23, comprising illuminating the self-expanding sinus dilator during the positioning thereof into the stenotic opening.

* * * * *

UNITED STATES PATENT AND TRADEMARK OFFICE

CERTIFICATE OF CORRECTION

PATENT NO. : 9,498,239 B2
APPLICATION NO. : 13/219497
DATED : November 22, 2016
INVENTOR(S) : Schreck et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 236 days.

Signed and Sealed this
Twenty-fifth Day of September, 2018

Andrei Iancu
*Director of the United States Patent and Trademark Office*